(12) United States Patent
Kumon et al.

(10) Patent No.: US 8,946,173 B2
(45) Date of Patent: Feb. 3, 2015

(54) CANCER CELL DEATH INDUCING AGENT HAVING EFFECTS OF POTENTIATING ANTICANCER DRUG AGAINST ANTICANCER-DRUG-RESISTANT CANCER

(75) Inventors: Hiromi Kumon, Okayama (JP); Yasutomo Nasu, Okayama (JP); Masami Watanabe, Okayama (JP); Yuji Kashiwakura, Okayama (JP); Kensuke Kawasaki, Okayama (JP)

(73) Assignee: Momotaro-Gene Inc., Okayama (JP)

( * ) Notice: Subject to any disclaimer, the term of this patent is extended or adjusted under 35 U.S.C. 154(b) by 685 days.

(21) Appl. No.: 12/734,488

(22) PCT Filed: Nov. 5, 2008

(86) PCT No.: PCT/JP2008/070541
§ 371 (c)(1),
(2), (4) Date: Jul. 15, 2010

(87) PCT Pub. No.: WO2009/060982
PCT Pub. Date: May 14, 2009

(65) Prior Publication Data
US 2011/0269824 A1    Nov. 3, 2011

(30) Foreign Application Priority Data
Nov. 5, 2007   (JP) .................................. 2007-287373

(51) Int. Cl.
| A61K 48/00 | (2006.01) |
| C12N 15/00 | (2006.01) |
| C12N 15/86 | (2006.01) |
| A61K 31/713 | (2006.01) |

(52) U.S. Cl.
CPC ............... *A61K 31/713* (2013.01); *A61K 48/00* (2013.01); *C12N 2710/10043* (2013.01)
USPC .......................... 514/44 R; 435/455; 435/456

(58) Field of Classification Search
CPC ................. A61K 31/713; A61K 48/00; C12N 2710/10043
USPC ................................. 435/455, 456; 514/44 R
See application file for complete search history.

(56) References Cited

U.S. PATENT DOCUMENTS

| 2006/0127482 A1 | 6/2006 | Fewell et al. |
| 2007/0280918 A1 | 12/2007 | Schwartz et al. |
| 2009/0005538 A1 | 1/2009 | Kumon et al. |

FOREIGN PATENT DOCUMENTS

| EP | 2090654 A1 | 8/2009 |
| WO | 01/38523 A1 | 5/2001 |
| WO | 2006/016062 A1 | 2/2006 |
| WO | 2006/062723 A1 | 6/2006 |
| WO | 2006/098074 A1 | 9/2006 |
| WO | 2008/050898 A1 | 5/2008 |

OTHER PUBLICATIONS

Gottesman et al., Annu. Rev. Med., 53: 615-27, 2002.*
Chinese Patent Office Action, issued Nov. 1, 2011 in Chinese Application No. 200880122369.2.
Abarzua et al., Adenovirus-Mediated Overexpression of REIC/Dkk-3 Selectivity Induces Apoptosis in Human Prostate Cancer Cells through Activation of c-Jun-NH2-Kinase, Cancer Research, 65(21):9617-9622 (2005).
Abarzua et al., "An N-terminal 78 amino acid truncation of REIC/Dkk-3 effectively induces apoptosis." Biochemical and Biophysical Research Communications (2008), vol. 375, pp. 614-618.
Edamura et al., "Adenovirus-mediated REIC/Dkk-3 gene transfer inhibits tumor growth and metastasis in an orthotopic prostate cancer model." Cancer Gene Therapy (2007), vol. 14, pp. 765-772.
Tanimoto et al., "REIC/Dkk-3 as a potential gene therapeutic agent against human testicular cancer." International Journal of Molecular Medicine (2007), vol. 19, pp. 363-368.
International Search Report issued on Dec. 22, 2008 in International Application No. PCT/JP2008/070541.
Kaku, Haruki et al, "The Present State and Future Strategies of Gene Therapy for Prostate Cancer in Okayama University." Nishinihon J. Urol. 69: (2007), pp. 221-229.
Abarzua, Fernando, "Fundamental Experiment on Gene Therapy for Human Prostate Cancer Using REIC/Dkk-3 Gene." Journal of Okayama Medical Association (May 2007), vol. 119, pp. 21-26.
EPO Communication with Supplementary European Search Report issued in EPO Appln. 08847693, Dec. 7, 2011.
Kawasakai et al., Cancer Gene Therapy, vol. 16, No. 1, pp. 65-72 (on-line pub. Jul. 25, 2008).
Fujita et al., Int. J. Cancer, 117:670-682 (2005).

* cited by examiner

Primary Examiner — Thaian N Ton
(74) Attorney, Agent, or Firm — Fitch, Even, Tabin & Flannery LLP

(57) ABSTRACT

The present invention provides a drug capable of causing cancer cells to restore anticancer drug sensitivity in cases in which cancer has acquired resistance to an anticancer drug and inducing cell death in cancer cells. The present invention specifically provides a cancer cell death inducing agent comprising REIC/Dkk-3 DNA as an active ingredient and having effects of potentiating an anticancer drug for cancer cells having anticancer drug resistance.

3 Claims, 15 Drawing Sheets
(5 of 15 Drawing Sheet(s) Filed in Color)

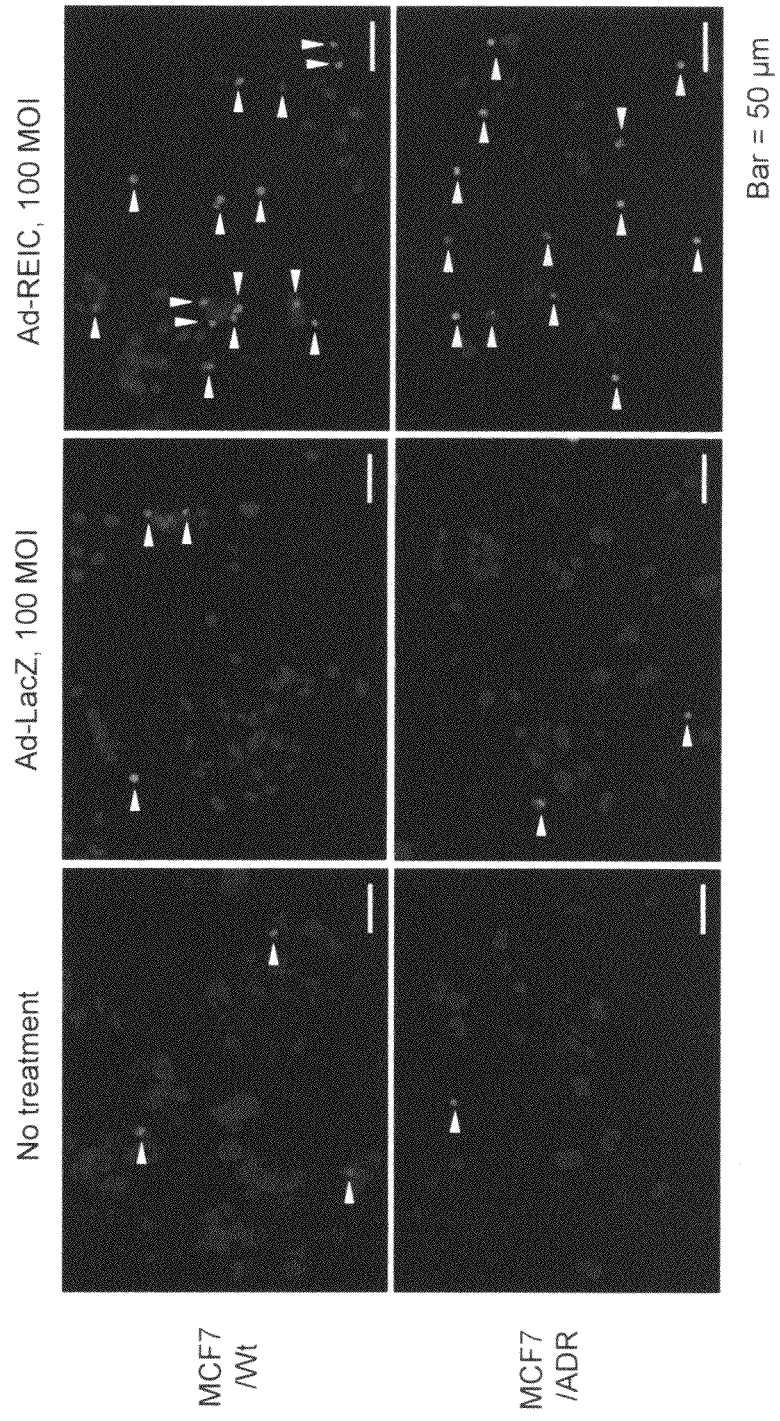

CANCER CELL DEATH INDUCING AGENT HAVING EFFECTS OF POTENTIATING ANTICANCER DRUG AGAINST ANTICANCER-DRUG-RESISTANT CANCER

CROSS REFERENCE TO RELATED APPLICATION

This application is a U.S. National Stage entry of International Application No. PCT/JP2008/070541 filed on Nov. 5, 2008, which claims priority to Japanese Application No. 2007-287373, filed on Nov. 5, 2007. The complete disclosures of the referenced international and priority application, including any sequence listings, are incorporated herein by reference.

TECHNICAL FIELD

The present invention relates to a pharmaceutical composition for treatment of anticancer-drug-resistant cancer.

BACKGROUND ART

Factors having effects on sensitivity and/or resistance of cancer cells to anticancer drugs are changes in a mechanism for excretion of such drug extracellularly, drug metabolism, DNA repair, PI3K-Akt pathway, and apoptotic pathway, for example. In particular, it is known that in many anticancer-drug-resistant cancer cells, accumulation of anticancer drugs decreases, and the expression of P-glycoprotein actively pumping out wide-ranging anticancer drugs extracellularly or of a multidrug (anticancer drug) resistance-related protein, MRP1, increases in cell membranes. Several examples of conventional techniques have been reported, such as the in vitro introduction of a gene encoded to attenuate P-glycoprotein expression into anticancer-drug-resistant cancer cells, so as to attenuate the anticancer drug resistance of the cells (Masuda Y. et al., Cancer Chemother Pharmacol. 1998; 42(1): 9-16; Wang F S. et al., Hum Gene Ther. 1999 May 1; 10 (7): 1185-95; Yague E. et al., Gene Ther. 2004 July; 11 (14): 1170-4). However, examples reported herein are the results of in vitro experiments, and in vivo usefulness has never been demonstrated with the use of animals. Also, even after the above reports, confirmation of the effects in vivo has never been reported.

Meanwhile, a REIC/Dkk-3 gene is known as a cell-immortalization-related gene. It has been reported that the expression of this gene is suppressed in cancer cells (International Patent Publication WO01/038523 Pamphlet; Tsuji, T. et al., BiochemBiophys Res Commun 268, 20-4 (2000); Tsuji, T. et al., BiochemBiophys Res Commun 289, 257-63 (2001); Nozaki, I. et al., Int J Oncol 19, 117-21 (2001); Kurose, K. et al., J Urol 171, 1314-8 (2004)).

The REIC/Dkk-3 gene is a member of the Dkk family, and it has been suggested that it inhibits Wnt signal transduction via a Wnt receptor (Bafico, A. et al., Nat Cell Biol 3, 683-6 (2001); Hoang, B. H. et al., Cancer Res 64, 2734-9 (2004)). It has been reported that the Wnt gene plays multiple roles in important biological events such as cell growth, differentiation, and canceration (Moon, R. T. et al., Science 296, 1644-6 (2002)). Therefore, the Dkk family (4 genes of which are currently known in humans) may be similarly responsible for important functions in cell growth, differentiation, and canceration, but most members thereof remain unelucidated.

Patent document 1 International Patent Publication WO01/038523 Pamphlet
Non-patent document 1 Masuda Y. et al., Cancer chemother Pharmacol. 1998; 42 (1): 9-16
Non-patent document 2 Wang F S. et al., Hum Gene Ther. 1999 May 1; 10 (7): 1185-95
Non-patent document 3 Yague E. et al., Gene Ther. 2004 July; 11 (14): 1170-4
Non-patent document 4 Tsuji, T. et al., BiochemBiophys Res Commun 268, 20-4 (2000)
Non-patent document 5 Tsuji, T. et al., BiochemBiophys Res Commun 289, 257-63 (2001)
Non-patent document 6 Nozaki, I. et al., Int J Oncol 19, 117-21 (2001)
Non-patent document 7 Kurose, K. et al., J Urol 171, 1314-8 (2004)
Non-patent document 8 Bafico, A. et al., Nat Cell Biol 3, 683-6 (2001)
Non-patent document 9 Hoang, B. H. et al., Cancer Res 64, 2734-9 (2004)
Non-patent document 10 Moon, R. T. et al., Science 296, 1644-6 (2002)

DISCLOSURE OF THE INVENTION

An object of the present invention is to provide a drug for causing cancer cells to restore anticancer drug sensitivity and inducing cell death in cancer cells of cancer having acquired anticancer drug resistance.

As described above, it has never been reported that a gene encoded to attenuate P-glycoprotein expression attenuates in vivo anticancer drug resistance. This strongly suggests that the effects of recovering anticancer drug sensitivity and the effects of tumor shrinkage upon the combined use of an anticancer drug have not been confirmed in vivo at levels that can be expected from in vitro results.

The present inventors administered Ad-REIC (prepared by introducing REIC/Dkk-3 DNA into an adenovirus vector) to cancer cells having resistance to an anticancer drug, doxorubicin (adriamycin). Thus, the present inventors discovered that the sensitivity of the cancer cells to the anticancer drug was recovered and the cell death (apoptosis) of the cancer cells was induced. This finding demonstrates that Ad-REIC has effects of causing cancer cells to restore sensitivity to an anticancer drug; that is, potentiating the action of the anticancer drug and thus inducing cell death in cancer.

Therefore, a cancer cell death inducing agent having effects of potentiating an anticancer drug in anticancer-drug-resistant cancer is expected to recover anticancer drug sensitivity in an in vivo animal model and/or to exert tumor shrinkage effects upon combined use with the anticancer drug in an in vivo animal model, as a result of the elimination of strong anticancer drug resistance based on the advantage of gene transfer efficiency achieved through the use of an adenovirus vector and the effects of inducing cancer cell death.

The present invention encompasses the following embodiments.

[1] A cancer cell death inducing agent having an effect of potentiating an anticancer drug for a cancer cell having anticancer drug resistance, comprising the following REIC/Dkk-3 DNA as an active ingredient:
(a) a DNA consisting of the nucleotide sequence shown in SEQ ID NO: 1;
(b) a DNA hybridizing under stringent conditions to a DNA consisting of a nucleotide sequence complementary to the nucleotide sequence shown in SEQ ID NO: 1 and encoding a protein having cell death inducing activity;

(c) a polynucleotide consisting of a nucleotide sequence that begins from the 1st nucleotide and terminates at any nucleotide between the 117th nucleotide and the 234th nucleotide in the nucleotide sequence shown in SEQ ID NO: 1; or
(d) a polynucleotide hybridizing under stringent conditions to a polynucleotide consisting of a nucleotide sequence complementary to the nucleotide sequence that begins from the 1st nucleotide and terminates at any nucleotide between the 117th nucleotide and the 234th nucleotide in the nucleotide sequence shown in SEQ ID NO: 1, and having cell death inducing activity.

[2] A cancer cell death inducing agent having an effect of potentiating an anticancer drug for a cancer cell having anticancer drug resistance, comprising a vector containing the following REIC/Dkk-3 DNA as an active ingredient:
(a) a DNA consisting of the nucleotide sequence shown in SEQ ID NO: 1;
(b) a DNA hybridizing under stringent conditions to a DNA consisting of a nucleotide sequence complementary to the nucleotide sequence shown in SEQ ID NO: 1, and encoding a protein having cell death inducing activity;
(c) a polynucleotide consisting of a nucleotide sequence that begins from the 1st nucleotide and terminates at any nucleotide between the 117th nucleotide and the 234th nucleotide in the nucleotide sequence shown in SEQ ID NO: 1; or
(d) a polynucleotide hybridizing under stringent conditions to a polynucleotide consisting of a nucleotide sequence complementary to a nucleotide sequence that begins from the 1st nucleotide and terminates at any nucleotide between the 117th nucleotide and the 234th nucleotide in the nucleotide sequence shown in SEQ ID NO: 1, and encoding a polypeptide having cell death inducing activity.

[3] The cancer cell death inducing agent having an effect of potentiating an anticancer drug according to [2], wherein the vector is an adenovirus vector.

[4] The cancer cell death inducing agent having an effect of potentiating an anticancer drug according to any one of [1] to [3], wherein the anticancer drug is an anticancer antibiotic.

[5] A cancer therapeutic drug for cancer resistant to an anticancer drug, containing the cancer cell death inducing agent having an effect of potentiating an anticancer drug according to any one of [1] to [4].

[6] A cancer therapeutic drug for cancer resistant to the above anticancer drug, which is a kit comprising an anticancer drug and the cancer cell death inducing agent according to any one of [1] to [4].

[7] The cancer therapeutic drug for cancer resistant to the anticancer drug according to [6], wherein the anticancer drug is an anticancer antibiotic.

[8] Use of the following REIC/Dkk-3 DNA or a vector containing the DNA in the manufacture of a cancer therapeutic drug for cancer resistant to an anticancer drug:
(a) a DNA consisting of the nucleotide sequence shown in SEQ ID NO: 1;
(b) a DNA hybridizing under stringent conditions to a DNA consisting of a nucleotide sequence complementary to the nucleotide sequence shown in SEQ ID NO: 1, and encoding a protein having cell death inducing activity;
(c) a polynucleotide consisting of a nucleotide sequence that begins from the 1st nucleotide and terminates at any nucleotide between the 117th nucleotide and the 234th nucleotide in the nucleotide sequence shown in SEQ ID NO: 1; or
(d) a polynucleotide hybridizing under stringent conditions to a polynucleotide consisting of a nucleotide sequence complementary to a nucleotide sequence that begins from the 1st nucleotide and terminates at any nucleotide between the 117th nucleotide and the 234th nucleotide in the nucleotide sequence shown in SEQ ID NO: 1, and encoding a polypeptide having cell death inducing activity.

[9] The use according to [8], wherein the vector is an adenovirus vector.

[10] The use according to [8] or [9], wherein the anticancer drug is an anticancer antibiotic.

[11] A REIC/Dkk-3 DNA for use in treatment with the use of a cancer therapeutic drug for cancer resistant to an anticancer drug, which is:
(a) a DNA consisting of the nucleotide sequence shown in SEQ ID NO: 1;
(b) a DNA hybridizing under stringent conditions to a DNA consisting of a nucleotide sequence complementary to the nucleotide sequence shown in SEQ ID NO: 1, and encoding a protein having cell death inducing activity;
(c) a polynucleotide consisting of a nucleotide sequence that begins from the 1st nucleotide and terminates at any nucleotide between the 117th nucleotide and the 234th nucleotide in the nucleotide sequence shown in SEQ ID NO: 1; or
(d) a polynucleotide hybridizing under stringent conditions to a polynucleotide consisting of a nucleotide sequence complementary to a nucleotide sequence that begins from the 1st nucleotide and terminates at any nucleotide between the 117th nucleotide and the 234th nucleotide in the nucleotide sequence shown in SEQ ID NO: 1, and encoding a polypeptide having cell death inducing activity.

[12] The REIC/Dkk-3 DNA according to [11], wherein a vector is an adenovirus vector.

[13] The REIC/Dkk-3 DNA according to [11] or [12], wherein the anticancer drug is an anticancer antibiotic.

[14] A vector containing the following REIC/Dkk-3 DNA for use in treatment with the use of a cancer therapeutic drug for cancer resistant to an anticancer drug:
(a) a DNA consisting of the nucleotide sequence shown in SEQ ID NO: 1;
(b) a DNA hybridizing under stringent conditions to a DNA consisting of a nucleotide sequence complementary to the nucleotide sequence shown in SEQ ID NO: 1, and encoding a protein having cell death inducing activity;
(c) a polynucleotide consisting of a nucleotide sequence that begins from the 1st nucleotide and terminates at any nucleotide between the 117th nucleotide and the 234th nucleotide in the nucleotide sequence shown in SEQ ID NO: 1; or
(d) a polynucleotide hybridizing under stringent conditions to a polynucleotide consisting of a nucleotide sequence complementary to a nucleotide sequence that begins from the 1st nucleotide and terminates at any nucleotide between the 117th nucleotide and the 234th nucleotide in the nucleotide sequence shown in SEQ ID NO: 1, and encoding a polypeptide having cell death inducing activity.

[15] A vector containing the REIC/Dkk-3 DNA according to [11], which is an adenovirus vector.

[16] A vector containing the REIC/Dkk-3 DNA according to [11] or [12], wherein the anticancer drug is an anticancer antibiotic.

[17] A cancer therapeutic drug kit for cancer resistant to an anticancer drug, comprising the following REIC/Dkk-3 DNA or a vector containing the DNA and an anticancer drug:
(a) a DNA consisting of the nucleotide sequence shown in SEQ ID NO: 1;
(b) a DNA hybridizing under stringent conditions to a DNA consisting of a nucleotide sequence complementary to the nucleotide sequence shown in SEQ ID NO: 1, and encoding a protein having cell death inducing activity;
(c) a polynucleotide consisting of a nucleotide sequence that begins from the 1st nucleotide and terminates at any nucleotide between the 117th nucleotide and the 234th nucleotide in the nucleotide sequence shown in SEQ ID NO: 1; or (d) a polynucleotide hybridizing under stringent conditions to a polynucleotide consisting of a nucleotide sequence complementary to a nucleotide sequence that begins from the 1st nucleotide and terminates at any nucleotide between the 117th nucleotide and the 234th nucleotide in the nucleotide sequence shown in SEQ ID NO: 1, and encoding a polypeptide having cell death inducing activity.

[18] The cancer therapeutic drug kit for cancer resistant to an anticancer drug according to [17], wherein the anticancer drug is an anticancer antibiotic.

[19] A method for causing a cancer cell having anticancer drug resistance to restore anticancer drug sensitivity and then inducing cancer cell death, comprising administering the following REIC/Dkk-3 DNA or a vector containing the DNA to a cancer cell having anticancer drug resistance.

[20] The method for inducing cancer cell death according to [19], wherein the vector is an adenovirus vector.

[21] The method for inducing cancer cell death according to [19] or [20], wherein the anticancer drug is an anticancer antibiotic.

[22] A method for treating a patient with cancer that is resistant to an anticancer drug, comprising administering the following REIC/Dkk-3 DNA or a vector containing the DNA to a patient with cancer resistant to an anticancer drug.

[23] The method for treating a patient with cancer that is resistant to an anticancer drug according to [22], wherein the vector is an adenovirus vector.

[24] The method for treating a patient with cancer that is resistant to an anticancer drug according to [21] or [22], wherein the anticancer drug is an anticancer antibiotic.

[25] The method for treating a patient with cancer resistant to an anticancer drug, comprising administering the following REIC/Dkk-3 DNA or a vector containing the DNA and the anticancer drug to a patient with cancer resistant to the anticancer drug.

[26] The method for treating a patient with cancer resistant to an anticancer drug according to [25], wherein the vector is an adenovirus vector.

[27] The method for treating a patient with cancer resistant to an anticancer drug according to [25] or [26], wherein the anticancer drug is an anticancer antibiotic.

This description includes part or all of the contents as disclosed in the description and/or drawings of Japanese Patent Application No. 2007-287373, which is a priority document of the present application.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 2A shows in vitro cell death induced by Ad-REIC in human mammary cancer cells. Specifically, FIG. 2A shows the results of Hoechst4452 staining of MCF7/Wt and MCF7/ADR cells after treatment.

FIG. 2B shows the cell death (%) of human primary mammary epithelial cell (HMEC) and mammary cancer cell lines after treatment.

BEST MODE FOR CARRYING OUT THE INVENTION

Figure 1:
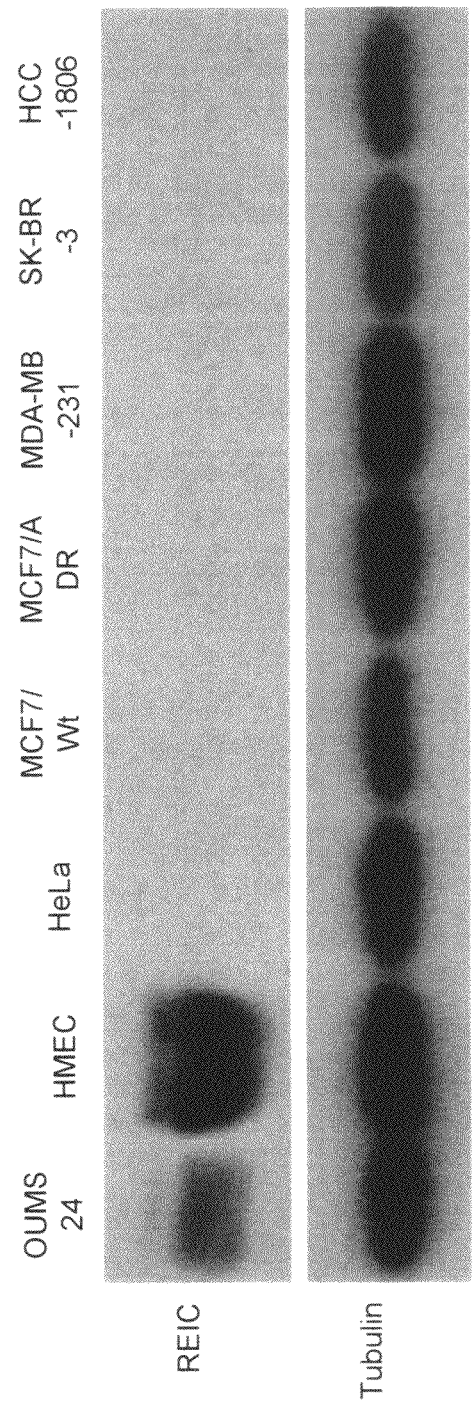
FIG. 1 shows the expression of REIC/Dkk-3 in human mammary cancer cell lines.

The present invention will be explained in detail as follows.

The cancer cell death (apoptosis) inducing agent having effects of potentiating an anticancer drug of the present invention comprises REIC/Dkk-3 DNA as an active ingredient.

The nucleotide sequence of the REIC/Dkk-3 DNA is shown in SEQ ID NO: 1. Also, the amino acid sequence of a REIC/Dkk-3 protein encoded by the REIC/Dkk-3 DNA is shown in SEQ ID NO: 2.

Also, REIC/Dkk-3 DNA contained in the cancer cell death inducing agent of the present invention having effects of potentiating an anticancer drug is a DNA encoding a protein having cancer cell death inducing activity, such as a DNA hybridizing under stringent conditions to a DNA having a nucleotide sequence complementary to the nucleotide sequence shown in SEQ ID NO: 1, a DNA having at least 85% or more, preferably 90% or more, further preferably 95% or more, and particularly preferably 97% or more identity with the nucleotide sequence shown in SEQ ID NO: 1, as calculated using BLAST (Basic Local Alignment Search Tool at the National Center for Biological Information) or the like (for example, using default; that is, initially set parameters), or a DNA encoding a protein comprising an amino acid sequence that has substitution, deletion, and/or addition of one, a plurality of, or several (1 to 10, preferably 1 to 5, further preferably 1 or 2) amino acids with respect to the amino acid sequence of the protein encoded by the above DNA. Here, the term "stringent conditions" refers to, conditions of approximately "1×SSC, 0.1% SDS, and 37° C.," for example. More stringent conditions are conditions of approximately "0.5× SSC, 0.1% SDS, and 42° C." Even more stringent conditions are conditions of approximately "0.2×SSC, 0.1% SDS, and 65° C." With the more stringent conditions for hybridization, isolation of DNA having high homology with a probe sequence can be expected. However, the above combinations of conditions of SSC, SDS, and temperature are merely exemplifications. Probe concentration, probe length, the reaction time for hybridization, and the like are adequately combined, so that required stringency can be realized. Moreover, REIC/Dkk-3 DNA contained in the cancer cell death inducing agent having effects of potentiating an anticancer drug according to the present invention is a DNA encoding the protein shown in SEQ ID NO: 2.

Furthermore, REIC/Dkk-3 DNA contained in the cancer cell death inducing agent of the present invention having effects of potentiating an anticancer drug is a nucleotide fragment, comprising a partial nucleotide sequence of the nucleotide sequence of the DNA. An example of such fragment is a nucleotide fragment that encodes a peptide having cell death inducing activity. Such nucleotide fragment can be easily obtained by cleaving the full-length REIC/Dkk-3 DNA at appropriate sites and then determining if the resultant has cell death inducing activity. Examples of such nucleotide fragment include: a polynucleotide consisting of a nucleotide sequence that begins from the $1^{st}$ nucleotide and terminates at any nucleotide between the $117^{th}$ nucleotide and the $234^{th}$ nucleotide in the nucleotide sequence of REIC/Dkk-3 DNA shown in SEQ ID NO: 1; and a polynucleotide hybridizing under stringent conditions to a polynucleotide consisting of a nucleotide sequence complementary to the nucleotide sequence that begins at the $1^{st}$ nucleotide and terminates at any nucleotide between the $117^{th}$ nucleotide and the $234^{th}$ nucleotide in the nucleotide sequence of REIC/Dkk-3 DNA shown in SEQ ID NO: 1 and encoding a polypeptide having cell death inducing activity. Examples of a polynucleotide consisting of the nucleotide sequence that begins at the $1^{st}$ nucleotide and terminates at any nucleotide between the $117^{th}$ nucleotide and the $234^{th}$ nucleotide in the nucleotide sequence of REIC/Dkk-3 DNA shown in SEQ ID NO: 1 include a polynucleotide (SEQ ID NO: 3) consisting of a sequence ranging from the $1^{st}$ nucleotide to the $117^{th}$ nucleotide and a polynucleotide (SEQ ID NO: 4) consisting of a sequence ranging from the $1^{st}$ nucleotide to the $234^{th}$ nucleotide.

REIC/Dkk-3 DNA can be obtained from human cells, human tissues, and the like based on the sequence information of SEQ ID NO: 1. Also, the REIC/Dkk-3 DNA can be obtained according to the description of WO01/038523.

Moreover, the present invention also encompasses a vector containing REIC/Dkk-3 DNA. The vector is introduced into a subject and then the REIC/Dkk-3 protein is expressed in vivo in the subject, so that the protein can exert the effects of inducing cancer cell death while having the effects of potentiating an anticancer drug.

A target gene (DNA) for gene therapy can be introduced into a subject by a known method. Examples of a method for introducing such gene into a subject include methods using viral vectors and methods using non-viral vectors. Various methods are known (Experimental Medicine, Separate Volume, Basic Technology for Gene Therapy, YODOSHA, 1996; Experimental Medicine, Separate Volume, Gene Transfer & Experimental Methods for Expression Analysis, YODOSHA, 1997; Ed., Japan Society of Gene Therapy, Handbook for Development and Research of Gene Therapy (*Idenshi Chiryo Kaihatsu Kenkyu Handbook*), NTS, 1999).

A representative example thereof is a method that uses a viral vector, such as an adenovirus, adeno-associated virus, or retrovirus as a viral vector for gene transfer. A target gene can be introduced intracellularly by introducing a target gene into a DNA virus or RNA virus such as a retrovirus, herpes virus, vaccinia virus, poxvirus, poliovirus, sindbisvirus, Sendai virus, SV40, or immunodeficiency virus (HIV) that has been rendered nontoxic and then infecting cells with the recombinant virus.

When a gene according to the present invention is used for gene therapy using virus, an adenovirus vector is preferably used. The adenovirus vector is characterized in that: (1) it allows a gene to be introduced into many types of cell, (2) it allows a gene to be efficiently introduced even into cells at the stationary phase, (3) it makes condensation possible by centrifugation, so that high-titer (10 PFU/ml to 11 PFU/ml or more) virus can be obtained; and (4) it is suitable for direct gene transfer in vivo into tissue cells. As adenoviruses for gene therapy, the $1^{st}$ generation adenovirus vector prepared by deleting the E1/E3 region (Miyake, S., et al., Proc. Natl. Acad. Sci. U.S.A., 93, 1320, 1996), the $2^{nd}$ generation adenovirus vector prepared by deleting the E2 or E4 region in addition to the E1/E3 region (Lieber, A., et al., J. Virol., 70, 8944, 1996; Mizuguchi, H. & Kay, M. A., Hum. Gene Ther., 10, 2013, 1999), and the $3^{rd}$ generation adenovirus vector (GUTLESS) prepared by deleting the adenovirus genome almost completely (Steinwaerder, D. S., et al., J. Virol., 73, 9303, 1999) have been developed. Any adenovirus vector can be used for introducing a gene according to the present invention without particular limitation. Furthermore, an adeno-AAV hybrid vector prepared by imparting incorporation ability to the AAV chromosome (Recchia, A., et al., Proc. Natl. Acad. Sci. U.S.A., 96, 2615, 1999) or an adenovirus vector that is capable of incorporation into a chromosome with the use of a transposon gene can be used, for example. Such adenovirus vector can also be used to achieve long-term gene expression. Also, a peptide sequence having tissue-specific transferability to an H1 loop of an adenovirus fiber is inserted, so that tissue specificity can also be imparted to the adenovirus vector (Mizuguchi, H. & Hayakawa, T., *Nippon Rinsho*, 7, 1544, 2000).

In the present invention, an adenovirus vector containing REIC/Dkk-3 DNA is referred to as Ad-REIC.

Also, without the use of the above viruses, a target gene can be introduced into cells or tissues using a recombinant expression vector prepared by incorporating a gene expression vector such as a plasmid vector thereinto. For example, a gene can be introduced into cells by a lipofection method, a phosphoric acid-calcium coprecipitation method, a DEAE-dextran method, a direct injection method for DNA using a microglass tube, or the like. A recombinant expression vector can also be incorporated into cells by a gene transfer method using internal liposome, a gene transfer method using electrostatic type liposome, an HVJ-liposome method, an improved HVJ-liposome method (HVJ-AVE liposome method), a method using an HVJ-E (envelope) vector, a receptor-mediated gene transfer method, a method for transferring a DNA molecule together with a carrier (metal particle) into cells using a particle gun, a method for directly introducing naked-DNA, an introduction method using various polymers, or the like. Any expression vector can be used for these cases, as long as it enables the expression of a target gene in vivo. Examples of such expression vector include pCAGGS (Gene 108, 193-200 (1991)), pBK-CMV, pcDNA3, 1, pZeoSV (Invitrogen Corporation, stratagene), and pVAX1.

A vector comprising REIC/Dkk-3 DNA may further comprise a promoter and an enhancer for appropriate gene transcription, a poly A signal, a marker gene for labeling and/or selection of cells transfected with a gene, and the like. As a promoter in such case, a known promoter can be used.

For introduction of the cancer cell death inducing agent of the present invention comprising REIC/Dkk-3 DNA and having effects of potentiating an anticancer drug into a subject, an in vivo method that involves direct introduction of a gene therapeutic agent or an ex vivo method that involves extracting a type of cell from a human, introducing ex vivo a gene therapeutic agent into the cell, and then returning the cell into the body can be employed, for example (NIKKEI SCIENCE, Inc., 1994 April Issue, p. 20-45; The Pharmaceuticals Monthly, 36(1), 23-48 (1994); Extra Edition, Experimental Medicine, 12 (15), (1994); Ed., Japan Society of Gene Therapy, Handbook for Development and Research of Gene Therapy (*Idenshi Chiryo Kaihatsu Kenkyu Handbook*), NTS, 1999).

The cancer cell death inducing agent of the present invention comprising REIC/Dkk-3 DNA and having effects of potentiating an anticancer drug can be used as a therapeutic drug against cancer that is resistant to the anticancer drug.

In the present invention, the term "effects of potentiating an anticancer drug" means to attenuate the anticancer drug resistance of cancer and to maintain the anti-cancer activity of the anticancer drug. Specifically, the cancer cell death inducing agent of the present invention having effects of potentiating an anticancer drug causes cancer to restore its sensitivity to an anticancer drug and thus induces cancer cell death.

Examples of anticancer drugs to be targeted by the present invention include: anticancer antibiotics such as adriamycin (doxorubicin), dactinomycin, actinomycin D, chromomycin, daunomycin, bleomycin, peplomycin, donorubicin, epirubicin, and mitomycin C; alkylating agents such as a nitrosourea agent, nitrogen mustard (e.g., cyclophosphamide), dacarbazine, carmustine (BCNU), busulfan, ifosfamide, nimustine hydrochloride, lomustine (CCNU), and ranimustine (MCNU); antimetabolites such as methotrexate, aminopterin, 6-mercaptopurine, 5-fluorouracil, carmofur, cytarabine, hydroxy carbamide, and gemcitabine; plant alkaloid agents such as vinblastine, vincristine, paclitaxel, docetaxel, CPT-11 (irinotecan), and etoposide; hormonal agents; substances that modify biological functions, such as lentinan, picibanil, and bestatin; procarbazine; cisplatin; and carboplatin. Examples thereof also include anti-androgen agents that suppress the functions of androgenic hormones, which are used for treatment of particularly prostatic cancer. Examples of anti-androgen agents include leuplin, casodex, odyne, prostal, estracyt, and honvan. Examples thereof further include molecular targeting drugs exerting anti-cancer effects using cancer cell-specific molecules as indices. Examples of molecular targeting drugs include: tyrosine kinase inhibitors such as imatinib mesylate, gefitinib, erlotinib, vandetanib, and sunitinib; Raf kinase inhibitors such as sorafenib; TNF-α inhibitors such as etanercept; and monoclonal antibodies such as rituximab, cetuximab, infliximab, trastuzumab, and bevacizumab.

Examples of cancer targeted by the present invention include brain•nerve tumor, skin cancer, gastric cancer, lung cancer, liver cancer, lymphoma•leukemia, colon cancer, pancreatic cancer, anal rectal cancer, esophageal cancer, uterine cancer, mammary cancer, adrenal cancer, renal cancer, renal pelvic and ureteral cancer, bladder cancer, prostatic cancer, urethral cancer, penile cancer, testicular cancer, bone tumor•bone sarcoma, leiomyoma, rhabdomyoma, and mesothelioma. In particular, mammary cancer and bladder cancer are preferred. Among these examples of cancer, the present invention is effective against cancer cases characterized by, after treatment that involves intravenous administration of an anticancer drug such as adriamycin, the presence of cancerous lesions against which the anticancer drug has attenuated to exert tumor shrinkage effects and cancer cases characterized by the presence of cancerous lesions against which the anticancer drug is clinically inferred to exert no effects of tumor shrinkage.

The cancer cell death inducing agent of the present invention having effects of potentiating an anticancer drug causes endoplasmic reticulum stress in cancer cells. The endoplasmic reticulum stress induces JNK activation, P-glycoprotein concentration decreases as a result, and then the function of excreting the anticancer drug decreases in cells, so that the anticancer drug is thought to induce cancer cell death even at a lower concentration thereof. Furthermore, through mediation of induction of endoplasmic reticulum stress and JNK activation, a wide range of cytotoxic signals within cells can function to eliminate the anticancer drug resistance.

The cancer cell death inducing agent of the present invention having effects of potentiating an anticancer drug comprises REIC/Dkk-3 DNA or a vector containing the DNA as well as a pharmacologically acceptable carrier, a diluent, or an excipient.

The cancer cell death inducing agent of the present invention having effects of potentiating an anticancer drug can be administered in various forms, such as tablets, capsules, granules, powders, or syrups via oral administration, or injection preparations, drops, suppositories, sprays, eye drops, transnasal preparations, or adhesive preparations via parenteral administration.

The cancer cell death inducing agent of the present invention having effects of potentiating an anticancer drug can also be topically administered. For example, the cancer cell death inducing agent can exert its effects through administration thereof via injection to a cancer site or the like.

Preferably, the agent is directly injected into a local cancer lesion once or several times so that the agent is spread throughout the cancer lesion. Before and after injection, treatment that involves intravenous administration of an anticancer drug such as adriamycin is performed.

The present invention also encompasses a pharmaceutical composition comprising an anticancer drug and the cancer cell death inducing agent having the effects of potentiating the anticancer drug in combination. Specifically, the present invention encompasses: a cancer therapeutic drug that is a kit comprising an anticancer drug and REIC/Dkk-3 DNA; and a pharmaceutical composition for cancer treatment comprising an anticancer drug and REIC/Dkk-3 DNA.

The cancer cell death inducing agent of the present invention having effects of potentiating an anticancer drug contains a carrier, a diluent, and an excipient that are generally used in the field of preparations. For example, as a carrier for tablets or an excipient, lactose, magnesium stearate, or the like is used. As an aqueous solution for injection, saline, an isotonic solution containing dextrose, and another adjuvant is used, for example. An appropriate solubilizing agent such as alcohol, polyalcohol such as propylene glycol, a nonionic surfactant, or the like may also be used in combination. As an oily fluid, sesame oil, soybean oil, or the like is used. As a solubilizing agent, benzyl benzoate, benzyl alcohol, or the like may also be used in combination.

The dose differs depending on symptoms, age, body weight, and the like. Administration may be carried out once per several days or several weeks or several months, in an amount ranging from 0.001 mg to 100 mg via subcutaneous injection, intramuscular injection, or intravenous injection.

The cancer cell death inducing agent of the present invention having effects of potentiating an anticancer drug may be administered to a cancer patient affected by a cancer type above, who has a cancer lesion confirmed to show resistance to treatment with an anticancer drug.

The cancer cell death inducing agent of the present invention having effects of potentiating an anticancer drug is confirmed to exert the effects of cancer cell death-tumor shrinkage even in the case of single-agent administration. Furthermore, combined use of this agent and an anticancer drug doubly induces anti-cancer effects, so that strong effects of tumor shrinkage are expected.

Hereafter, the present invention is described in greater detail with reference to the following examples, although the present invention is not limited thereto.

EXAMPLE 1

Effects of REIC/Dkk-3 on Anticancer-Drug-Resistant Mammary Cancer Cells

In these Examples, examination was conducted by the following method using the following materials.

Cells and Cell Culture

Cell lines used in the Examples of the present invention were human mammary cancer cell lines MCF7/Wt (wild-type), MDA-MB-231, SK-BR-3, and HCC1806 and HeLa which is a human uterine cancer cell line. These cell lines were obtained from the ATCC (American Type Culture Collection). The anticancer-drug-resistant mammary cancer cell line (multidrug-resistant mammary cancer cell line) MCF7/ADR was provided by Dr. K. H. Cowan, the Eppley Institute for Research in Cancer and Allied Diseases, University of Nebraska, Medical Center (Batist G et al. J Biol Chem 1986; 261: 15544-15549). As control cells, human fibroblasts and OUMS24 were used. They were established by the present inventors (Bai L et al. Int J Cancer 1993; 53:451-456). Cell lines were each cultured using the following culture solutions.

OUMS24 was cultured under conditions of 5% $CO_2$ using Dulbecco's Modified Eagle Medium (Invitrogen) supplemented with 10% (v/v) fetal calf serum, penicillin (100 IU/ml), and streptomycin (100 μg/ml). MCF7/ADR was cultured using RPMI-1640 medium (Sigma) supplemented with 10% (v/v) fetal calf serum, penicillin (100 IU/ml), streptomycin (100 μg/ml), and 10 μM doxorubicin (adriacin (Trademark, Kyowa Hakko Kirin Co., Ltd.)). The other cell lines were cultured using RPMI-1640 medium supplemented with 10% (v/v) fetal calf serum, penicillin (100 IU/ml), and streptomycin (100 μg/ml).

Western Blot Analysis

Protein expression was examined by Western blot. Cells were washed twice with PBS and then protein extraction was carried out using a lysis buffer (50 mM HEPES, pH 7.4, 250 mM NaCl, 1 mM EDTA, 1% NP-40, 1 mM DTT, 1 mM PMSF, 5 μg/ml leupeptin, 5 μg/ml aprotinin, 2 mM $Na_3VO_4$, 1 mM NaF, and 10 mM β-GP). After centrifugation, a protein level in a supernatant was adjusted. Each resultant was diluted with 2×SDS sample buffer in an amount equivalent thereto and then heated at 95° C. for 5 minutes. Each sample (10 μg of a protein) was subjected to electrophoresis with 7.5% SDS-PAGE gel and then the resultant was transferred to a PVDF membrane. Blocking was carried out at room temperature for 1 hour using Tris buffered saline (TBS) containing 10% fat-free milk powder, 6% glycine, and 0.1% Tween-20. Primary antibodies used herein were: an anti-human REIC/Dkk-3 antibody (1:1000); an anti-JNK antibody sc-571 (1:500) (Santa Cruz Biotechnology); an anti-c-Jun antibody sc-1694 (1:500) (Santa Cruz Biotechnology); an anti-phosphorylated JNK antibody #9255 (1:500) (Cell Signaling Technology); an anti-phosphorylated c-Jun antibody #9261 (1:500) (Cell Signaling Technology); an anti-cleavage caspase-3 antibody #9661 (1:500) (Cell Signaling Technology); an anti-tubulin antibody T5168 (1:8000) (Sigma); and an anti-P-glycoprotein antibody C219 (1:250) (Calbiochem). After sufficient washing with TBS (T-TBS) and 0.1% Tween-20, a horseradish peroxidase-conjugated secondary antibody was added. Furthermore, after sufficient washing using T-TBS, color development was carried out by an enhanced chemiluminescence detection method (ECL kit). One (1) μM JNK inhibitor SP600125 (A. G. Scientific, Inc.) was added to some samples, so as to inhibit the kinase activity of JNK.

Construction of Adenovirus Vector (Ad-REIC) Containing REIC/Dkk-3 DNA

Full-length REIC/Dkk-3 cDNA was introduced into a cosmid vector pAxCAwt and then the resultant was transferred by the COS-TPC method (Takara Bio) to an adenovirus vector (Abarzua F et al. Cancer Res 2005; 65:9617-9622). An adenovirus vector (Ad-LacZ) containing a LacZ gene was used as a control.

Cell Death (Apoptosis) Assay

To examine in vitro cell death induction, cells were seeded in a 6-well flat bottom plate and then cultured for 24 hours. Cells were treated with Ad-LacZ and Ad-REIC at various MOIs (multiplicities of infection) in serum free medium for 2 hours and then the medium was exchanged with fresh complete medium. After 48 hours of incubation, an Hoechst33342 stock solution was added at a concentration of 2 μg/ml. Cells were incubated under dark conditions for 10 minutes. Hoechst33342 is an intercalater staining reagent, with which a total amount of chromatin and the degree of condensation of chromatin can be examined (Belloc F et al., Cytometry 1994; 17: 59-65, Maciorowski Z et al., Cytometry 1998; 32: 44-50). Death of cells having highly condensed and fragmented nuclei was observed using a fluorescence microscope and then such cells were identified. Such cells confirmed to have undergone cell death in 3 to 5 different visual fields were counted under a microscope.

To detect in vivo cells for which cell death had been confirmed, TUNEL (terminal deoxynucleotidyltransferase-mediated UTP end labeling) assay was carried out using a Fluorescein In Situ Cell Detection Kit (Roche). Specifically, tumor tissues were cut into sections and each section was added into an OCT compound and then rapidly frozen in liquid nitrogen. Each frozen section sample (10 μm) was fixed with methanol at room temperature for 30 minutes, washed, impregnated with PBS containing 0.1% Triton X-100, and then stained with a TUNEL reaction mixture.

Cell Survival Rate Assay

Cells were seeded in a 96-well flat bottom microplate at 1000 cells per well. After 24 hours of incubation, cells were treated with Ad-LacZ and Ad-REIC at 100 MOI in serum free medium for 2 hours, followed by exchange with fresh complete medium. After 48 hours, floating dead cells were removed by medium exchange. Adhering cells were cultured with doxorubicin at various concentrations for 72 hours. At the end of incubation, cell survival rates were measured using CellTiter96 (trademark) Aqueous One Solution Cell Proliferation Assay (Promega Corp.).

Detection and Quantitative Determination of Intracellular Accumulation of Doxorubicin Cells were seeded in a 6-well flat bottom plate and then cultured for 24 hours. After 24 hours of incubation, cells were treated with Ad-LacZ and Ad-REIC at 100 MOI in serum free medium for 2 hours, followed by exchange with fresh complete medium. After 48 hours, floating dead cells were removed by medium exchange, adhering cells were cultured with 10 μM doxorubicin for 36 hours. At the end of incubation, the red autofluorescence of doxorubicin was observed and scanned. Scanned images were subjected to quantitative determination of the accumulation density of doxorubicin using Scion Image (Scion Corp).

Xenograft Model

Female athymic (nu/nu) mice of 5-6 weeks of age were obtained from Charles River Laboratories International, Inc. On day 3 before injection of tumor cells, 17β estradiol pellets (SE-121, Innovative Research of America) were grafted in the right shoulder region of each mouse via subcutaneous injection. MCF7/Wt cells ($5 \times 10^6$ cells/0.1 ml PBS) were injected into the back on the left of each mouse and then a tumor was allowed to increase to 3 mm to 6 mm. Mice were divided randomly into 7 groups. Subsequently, $1.2 \times 10^8$ plaque forming units (PFU) of adenovirus vectors (Ad-LacZ and Ad-REIC) were adjusted with PBS to 0.1 ml and then the resultant was injected into the tumor. As a negative control, the same amount of PBS was injected. Tumor size was measured once every two weeks. Tumor volume was calculated by a formula (½×(w1×w2×w2); w1 represents the maximum diameter of a tumor and w2 represents the minimum diameter of a tumor) established by experiments.

Statistic Analysis

Data were expressed with average value±SE. Unpaired Student's t test was conducted for 2 groups. "P<0.05" was defined to indicate a significant difference. Analysis was conducted using a Statview 4.5 software program (Abucus concepts).

(1) Decreased REIC/Dkk-3 Gene Expression in Human Mammary Cancer Cell Lines

REIC/Dkk-3 protein expression in various cell lines was examined. Cell lines used herein were MCF7/Wt (wild-type), MDA-MB-231, SK-BR-3, and HCC1806 which are human mammary cancer cell lines as well as HeLa which is a human uterine cancer cell line. Human fibroblasts and OUMS24 were used as positive controls for expression (Abarzua F et al., Cancer Res 2005; 65: 9617-9622). In primary cultured human mammary cancer epithelial cells (HMEC) for which tubulin had been used as a loading control, the REIC/Dkk-3 protein was clearly observed between molecular weights of 60 kDa and 70 kDa. This accords with the result that a plurality of bands were observed corresponding to the REIC/Dkk-3 protein as analyzed by Western blot (Barzua F et al., Cancer Res 2005; 65: 9617-9622; Kurose K et al., J Urol 2004; 171: 1314-13181; Hsieh S Y, Oncogene 2004; 23: 9183-9189). FIG. 1 shows the results. FIG. 1 shows REIC/Dkk-3 expression in human mammary cancer cell lines. As shown in FIG. 1, bands indicating REIC/Dkk-3 expression were not observed in the cancer cell lines.

Figure 2B:
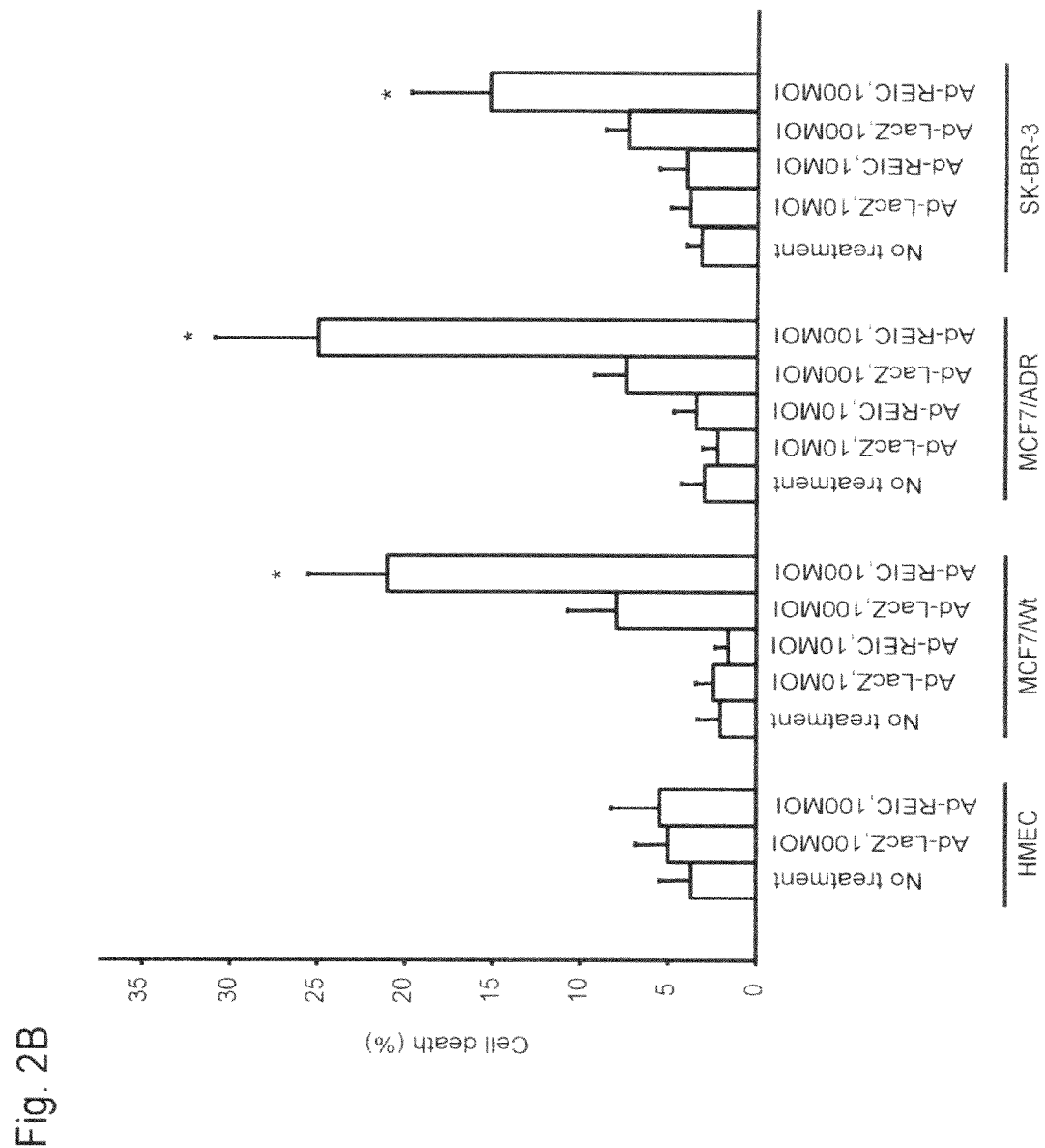
FIG. 2B shows in vitro cell death induced by Ad-REIC in human mammary cancer cells. Specifically.

(2) Induction of Cell Death of MCF7/Wt and MCF7/ADR Cells as a Result of Treatment with Ad-REIC Possible use of REIC/Dkk-3 for gene therapy for mammary cancer was examined by causing REIC/Dkk-3 overexpression in mammary cancer cell lines using Ad-REIC. The experiment was conducted 3 to 6 times. FIG. 2A and FIG. 2B show the results. As shown in FIG. 2A, cells that had died in cell death assay using Hoechst33342 were observed with high frequency in MCF7/Wt and MCF7/ADR treated with Ad-REIC. However, such cells were not observed in HMEC. Incidence (%) of cell death at 100 MOI was 5.5% in HMEC, 21.2% in MCF7/Wt, 25.0% in MCF7/ADR, and 15.2% in SK-BR-3 cells (FIG. 2B). When compared with treatment with control Ad-LacZ, treatment with Ad-REIC at 100 MOI significantly induced cell death in MCF7/Wt and MCF7/ADR cells. A significant difference (p<0.05) was observed between treatment with Ad-REIC and treatment with Ad-LacZ. In MDA-MB-231 cells, no difference in cell death induction was observed between Ad-REIC and the control.

Figure 3:
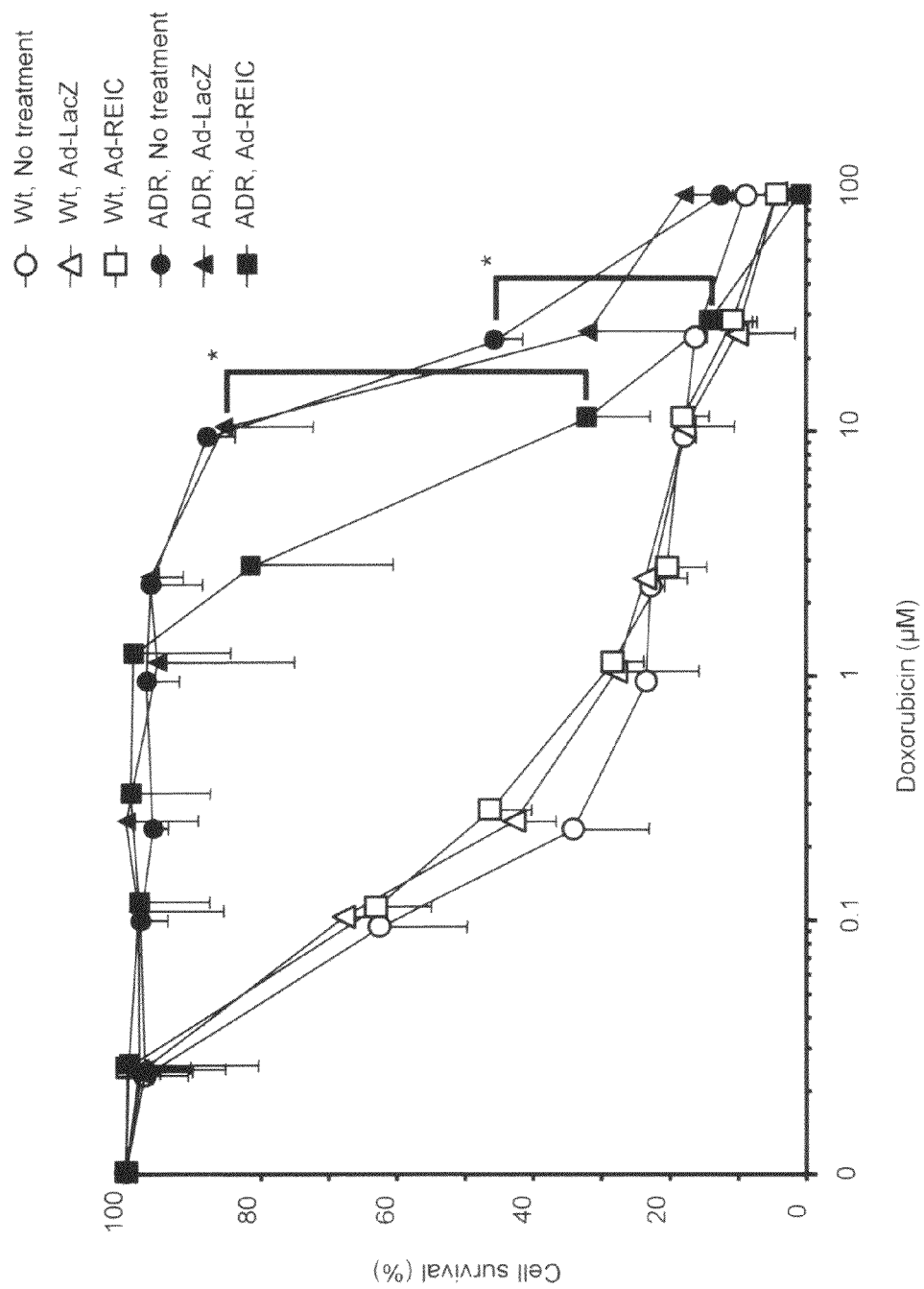
FIG. 3 shows the recovery of the sensitivity of MCF7/ADR cells to doxorubicin as a result of treatment with Ad-REIC.

(3) Increased Sensitivity of Multidrug-Resistant MCF7/ADR to Doxorubicin as a Result of Treatment with Ad-REIC The further usefulness of Ad-REIC in cancer therapy was examined using multidrug-resistant MCF7/ADR cells. MCF/Wt and MCF7/ADR cells were divided into 3 groups: a group of cells that were not treated, a group of cells treated with Ad-LacZ, and a group of cells treated with Ad-REIC. Cells were exposed to various concentrations of doxorubicin was evaluated, as was the ability of REIC/Dkk-3 overexpression to cause cells to restore drug resistance. MCF7/Wt cells were observed to show no significant difference that depended on treatment group. FIG. 3 shows the results. FIG. 3 shows dose-response curves (response to doxorubicin toxicity). As shown in FIG. 3, MCF7/ADR cells demonstrated a dose-response curve (response to doxorubicin toxicity) that significantly shifted to lower concentrations as a result of treatment with Ad-REIC. At 10 μM doxorubicin, cell survival % was 88.1% in the no treatment group, 85.6% in the group treated with Ad-LacZ, and 32.3% in the group treated with Ad-REIC. At 25 μM doxorubicin, cell survival rates were 45.9% in the no treatment group, 32.1% in the group treated with Ad-LacZ, and 14.3% in the group treated with Ad-REIC. Significant difference (p<0.05) was observed among treated groups.

Figure 4:
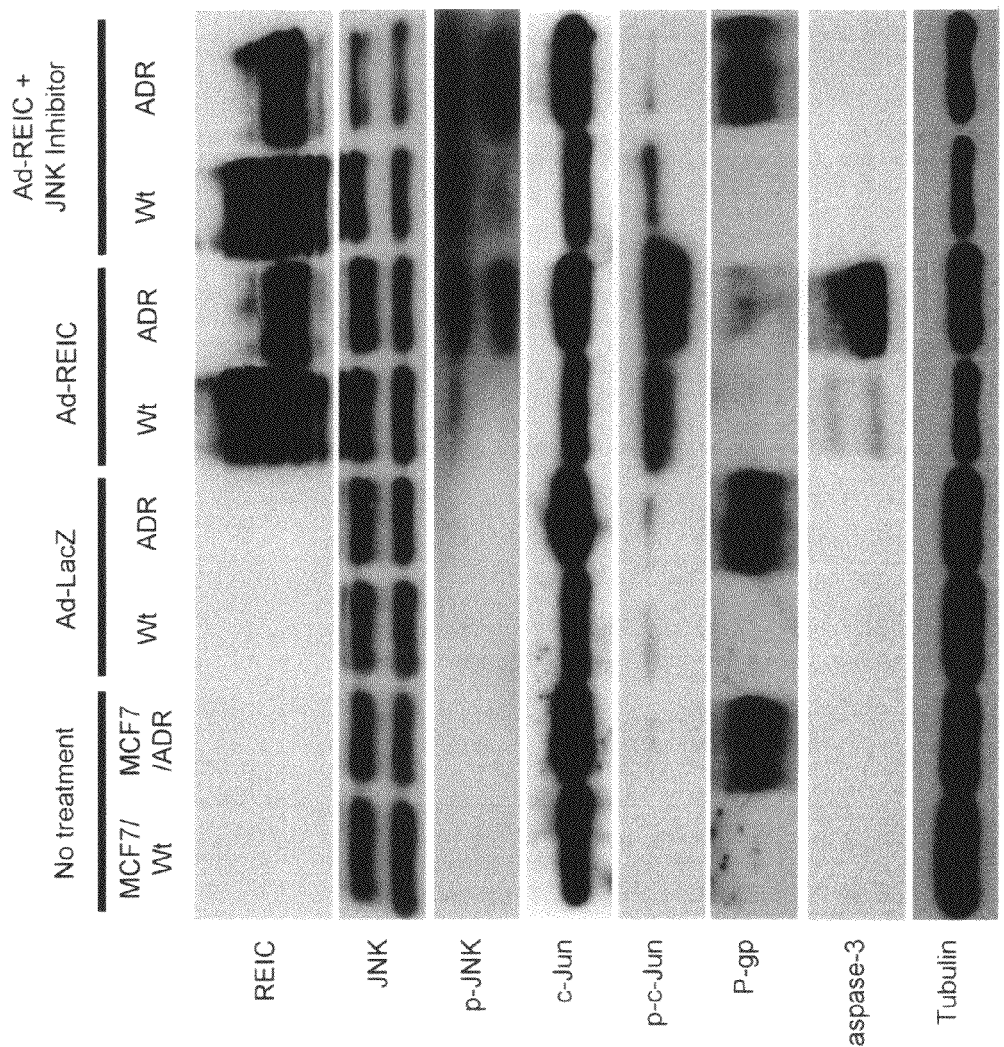
FIG. 4 shows downregulation of P-glycoprotein expression in MCF7/ADR cells in phosphorylated JNK-c-Jun-dependent manner as a result of treatment with Ad-REIC.

(4) Downregulation of P-Glycoprotein in MCF7/ADR Cells in Activated JNK-c-Jun-Dependent Manner as a Result of Treatment with Ad-REIC Expression levels of various proteins under REIC/Dkk-3 overexpression were measured by Western blot. Cells were treated with Ad-LacZ and Ad-REIC at 100 MOI. After 48 hours, floating dead cells were removed, adhering cells were lysed, and then the resultants were used as samples. To inhibit kinase activity of JNK in treatment with Ad-REIC, a 1 μM JNK inhibitor (SP600125) was added immediately after treatment with Ad-REIC. FIG. 4 shows the results. In FIG. 4, "p-" indicates phosphorylation and "P-gp" indicates P-glycoprotein. As a result of treatment with Ad-REIC, REIC/Dkk-3 protein expression was increased in both MCF7/Wt and MCF7/ADR cells. No changes in JNK level were observed in either type of cell subjected to any type of treatment. The C-Jun protein level in MCF7/ADR cells was greater than that in MCF7/Wt cells. After treatment with Ad-REIC, JNK activation in MCF7/Wt and MCF7/ADR cells was confirmed by detecting phosphorylation of c-Jun using a phosphorylated JNK-specific antibody. REIC/Dkk-3 overexpression significantly downregulated P-glycoprotein in MCF7/ADR cells. A JNK inhibitor, SP600125, is known to inhibit kinase activity of JNK, but not to inhibit phosphorylation of JNK itself (Bennett B L et al., Proc Natl Acad Sci U.S.A. 2001; 98: 13681-13686). The combined use of Ad-REIC and SP600125 caused no change in JNK activity. However, the expression level of phosphorylated c-Jun decreased and the P-glycoprotein level in MCF7/ADR cells was reversed. With respect to such change in P-glycoprotein expression, the level of cleaved caspase-3 in MCF7/Wt and MCF7/ADR cells was upregulated as a result of treatment with Ad-REIC and reversed by SP600125.

Figure 5A:
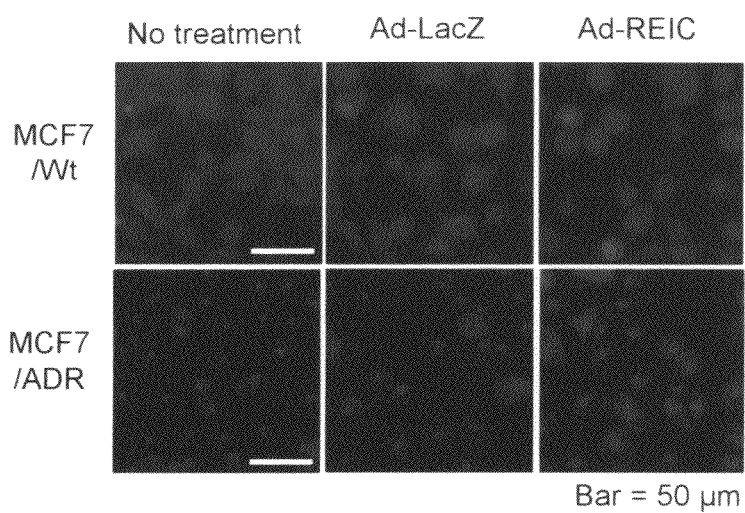
FIG. 5A shows fluorescence microscopic images showing intracellular accumulation of doxorubicin after treatment with Ad-REIC.
Figure 5B:
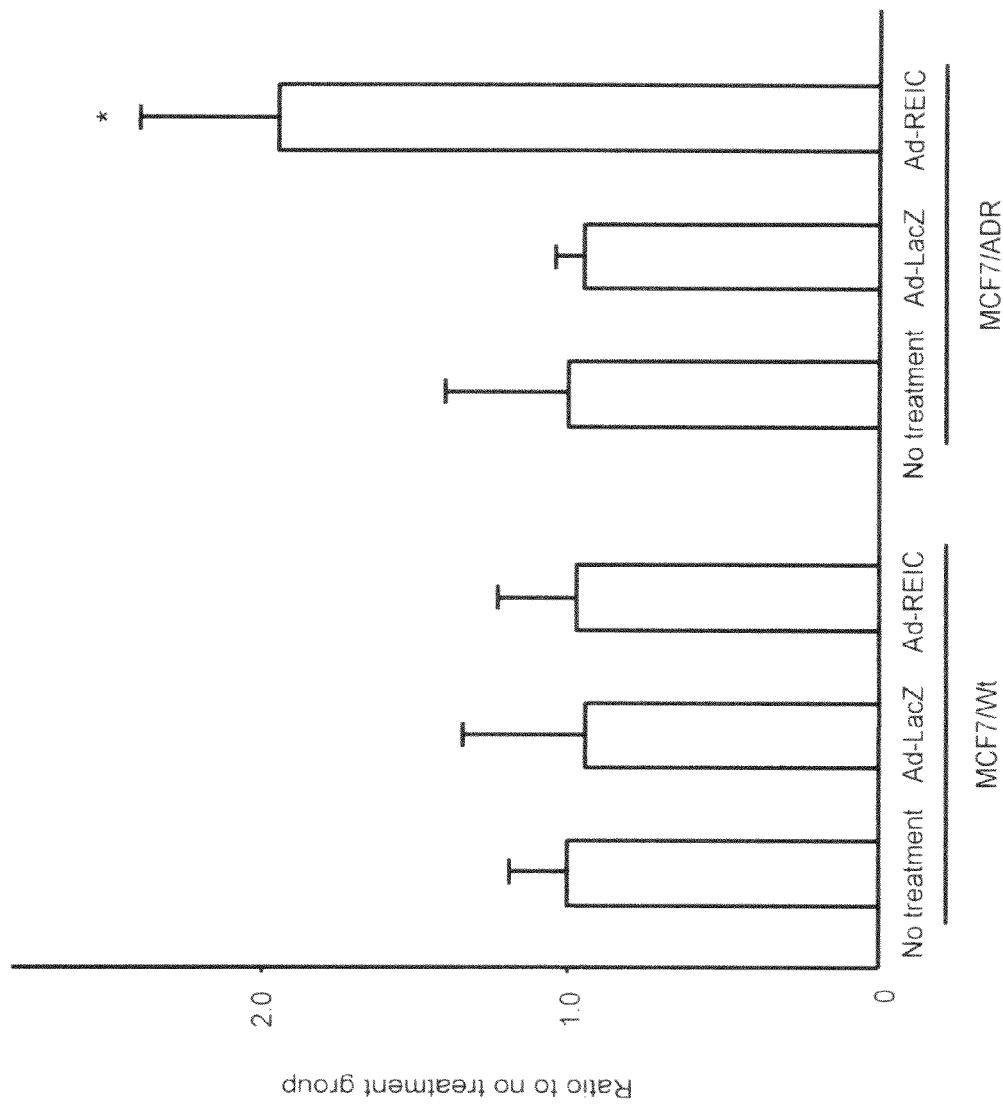
FIG. 5B shows intracellular accumulation of doxorubicin after treatment with Ad-REIC.

(5) Intracellular Accumulation of Doxorubicin as a Result of Treatment with Ad-REIC Intracellular accumulation of doxorubicin was examined at a concentration of 10 μM in order to examine the effects of treatment with Ad-REIC on doxorubicin kinetics in each type of cells. FIG. 5A and FIG. 5B show the results. FIG. 5A shows a representative example of fluorescence microscopic images of treated cells. FIG. 5B shows the results of randomly scanning red fluorescence and then quantitatively determining accumulation density. The mean value of untreated cells was adjusted to 1.0 in each cell line. As shown in FIG. 5A and FIG.

5B, treatment with Ad-REIC significantly increased intracellular accumulation of doxorubicin in MCF7/ADR cells such that the accumulation to twice as great an extent as that in the control group was observed. Significant difference (p<0.05) between treatment with Ad-REIC and treatment with Ad-LacZ was observed. In MCF7/Wt cells, no difference due to treatment was observed.

Figure 6A:
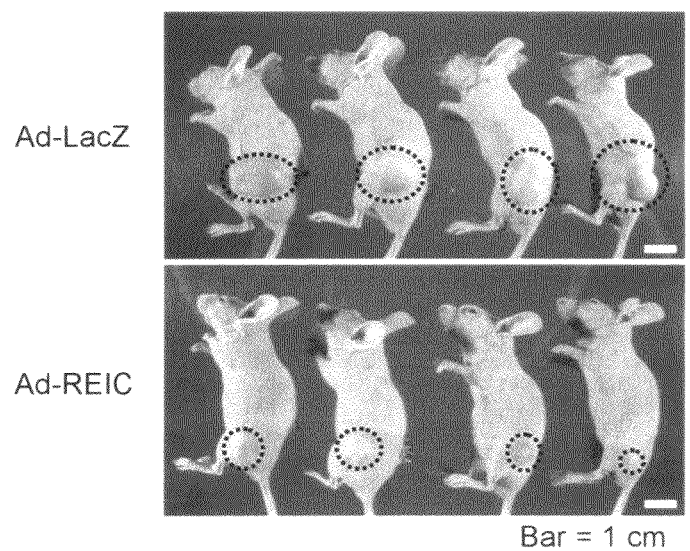
FIG. 6A shows the inhibitory effects of treatment with Ad-REIC on MCF/Wt tumor growth in nude mice.
Figure 6B:
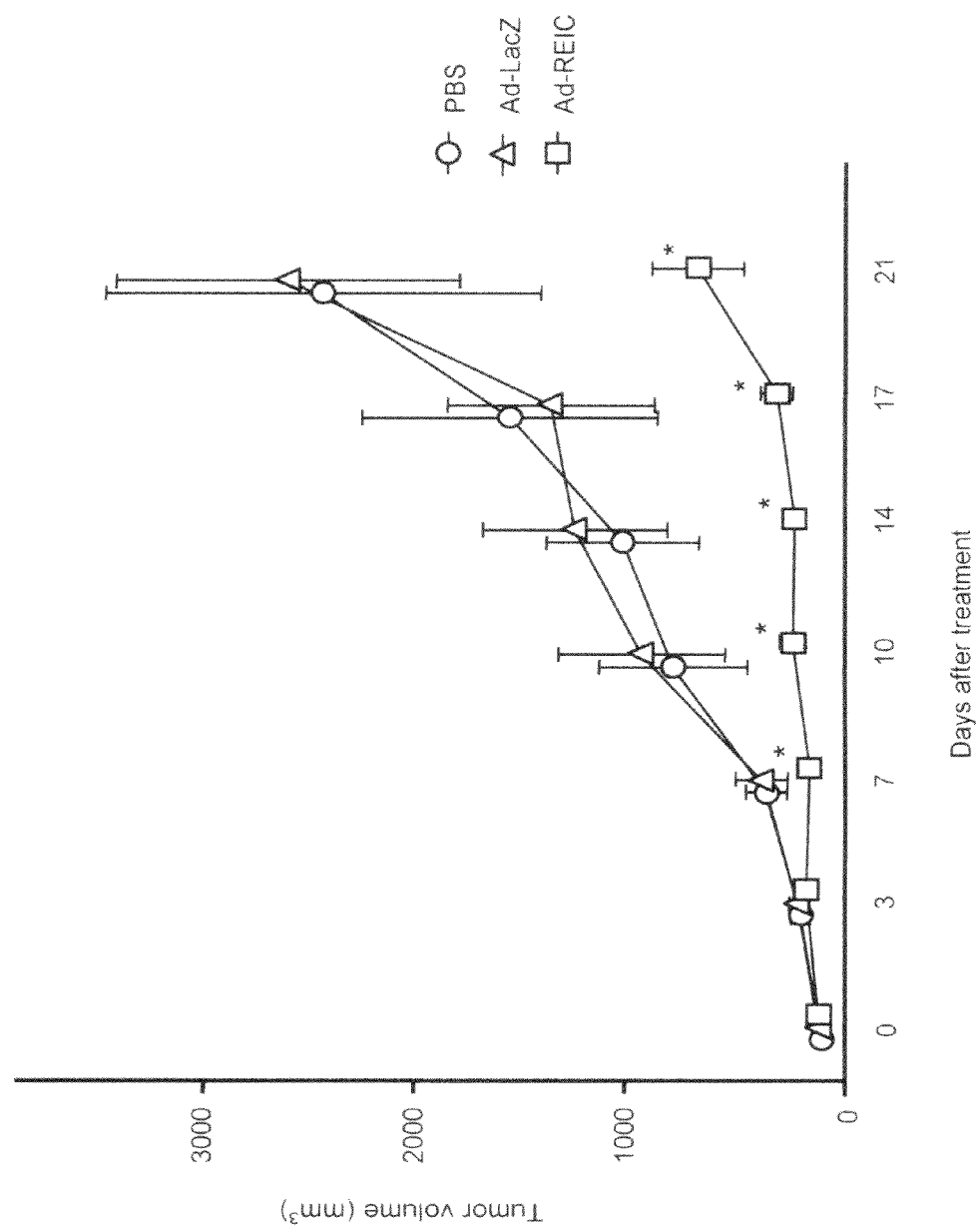
FIG. 6B shows tumor growth curves representing the inhibitory effects of treatment with Ad-REIC on MCF/Wt tumor growth in nude mice.
Figure 6C:
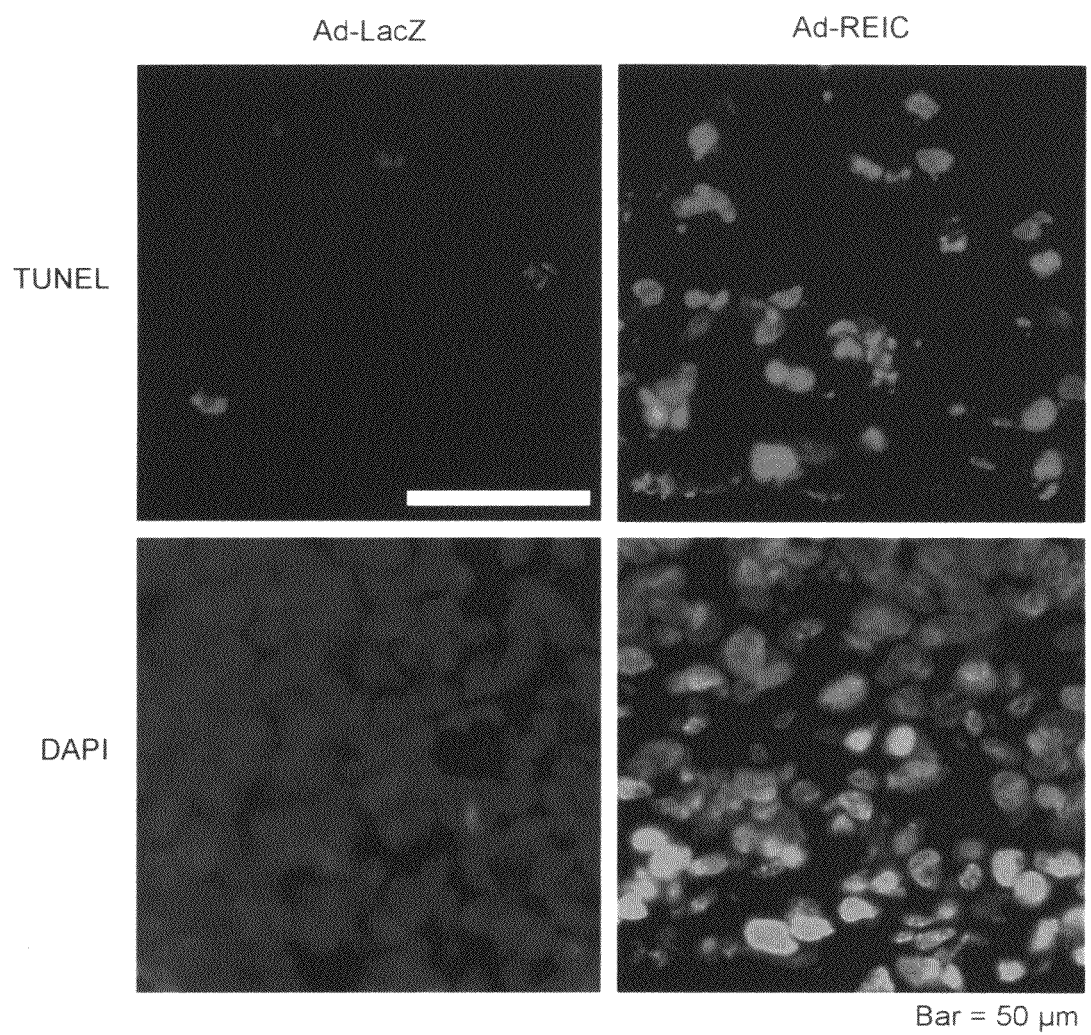
FIG. 6C shows the results of TUNEL staining of tumors collected on day 3 after administration of the virus to nude mice.

(6) Suppression of Mammary Cancer Growth in Mammary Cancer Xenograft Model as a Result of Intratumoral Treatment (Administration of) with Ad-REIC In vitro cell death induction due to REIC/Dkk-3 overexpression was confirmed in MCF/Wt cells. Next, in vivo antitumor effects of Ad-REIC were examined using a subcutaneous injection tumor model. FIG. 6A, FIG. 6B, and FIG. 6C show the results. FIG. 6A and FIG. 6B show the advent of xenografted tumor at the end of a 3-week observation period after treatment with Ad-LacZ and Ad-REIC. FIG. 6A shows photographic images showing nude mice in which tumors appeared. FIG. 6B shows tumor growth curves each produced by calculating the mean tumor volume in 7 mice per group. Significant difference (p<0.05) between treatment with Ad-REIC and treatment with Ad-LacZ was observed. FIG. 6C shows the results of TUNEL staining of tumors collected on day 3 after viral administration. Nuclei were stained by DAPI staining. As shown in FIG. 6B, tumor sizes were found to gradually increase during the 3-week observation period in the group to which PBS had been administered and the group to which Ad-LacZ had been administered. On the other hand, in the group treated with Ad-REIC, the tumor volume showed almost no change in 2 weeks, following which it gradually decreased. Significant differences were observed among the no treatment group, the group to which Ad-LacZ had been administered, and the group to which Ad-REIC had been administered from day 7 to week 3. To confirm REIC/Dkk-3 expression and the cell death effects of treatment with Ad-REIC, tumor tissues were excised on day 3 after vector administration. As shown in FIG. 6C, REIC/Dkk-3 overexpression was observed in tumors treated with Ad-REIC by Western blot. Subsequently, tumor sections were examined by TUNEL staining. Almost no cell death was observed in tumor sections to which Ad-LacZ had been administered. On the other hand, many TUNEL-positive cells were observed in tumor sections to which Ad-REIC had been administered.

It was demonstrated by this Example that REIC/Dkk-3 is useful for gene therapy against cancer. Adenovirus-mediated REIC/Dkk-3 overexpression induced cell death in mammary cancer cells and cell death took place in a JNK phosphorylation-dependent manner. MCF/Wt tumor growth inhibition in the mouse model can be explained by the effects of tumor cell death resulting from in vivo treatment with Ad-REIC. Furthermore, REIC/Dkk-3 overexpression downregulates P-glycoprotein expression through mediation of JNK activation in drug-resistant MCF7/ADR mammary cancer cells, so as to change the nature of the cell line from being resistant to the drug (doxorubicin) to being sensitive to the same.

The present inventors have previously reported that JNK activation resulting from administration of Ad-REIC plays a major role in cell death in various cancer cell lines (Abarzua F et al., Cancer Res 2005; 65: 9617-9622, Abarzua F et al., Int J Mol Med 2007; 20: 37-43; Tanimoto R et al., Int J Mol Med 2007; 19: 363-368). In prostatic cancer PC-3 cells, REIC/Dkk-3 overexpression activates JNK, decreases the Bcl-2 protein level, induces localization of the BaX protein in mitochondria, and then releases cytochrome C into the cytoplasm, thereby causing cell death (apoptosis) (Abarzua F et al., Cancer Res 2005, 65: 9617-9622).

In this Example, it was demonstrated that administration of Ad-REIC induced cell death in many mammary cancer cell lines (MCF7/Wt, MCF7/ADR, and SK-BR-3), but did not induce cell death in primary human mammary epithelial cells. Moreover, almost no REIC/Dkk-3 protein expression was observed in the mammary cancer cell lines, but REIC/Dkk-3 protein was abundant in primary epithelial cells. These results suggest that REIC/Dkk-3 overexpression selectively induces cell death in mammary cancer cells not expressing endogenous REIC/Dkk-3. This phenomenon is similar to phenomena noted in previous reports (Abarzua F et al., Cancer Res 2005, 65: 9617-9622; Abarzua F et al., Int J Mol Med 2007, 20: 37-43; Tanimoto R et al., Int J Mol Med 2007, 19: 363-368), suggesting that deletion or absence of REIC/Dkk-3 protein expression is important for cell death induction in cancer cells. Administration of Ad-REIC to cancer cells in which no REIC/Dkk-3 is present causes endoplasmic reticulum stress (ER stress) and then induces cell death in a JNK-dependent manner. Interestingly, overexpression of a certain kind of protein causes JNK activation induced by endoplasmic reticulum stress and cell death (Cudna R E, Biotechnol Bioeng 2003, 81: 56-65; Herr I. et al, Blood 2001, 98: 2603-2614). Accordingly, it is thought that REIC/Dkk-3 protein overexpression itself induces significant endoplasmic reticulum stress and then activates JNK in the endoplasmic reticula of cancer cells in which REIC/Dkk-3 protein expression is absent or unable to take place smoothly, so that cell death takes place.

P-glycoprotein plays a central role in excretion of anticancer drug, so as to increase cell survival against the anticancer drug. Also, upregulation of P-glycoprotein is an important mechanism by which cancer cells become resistant to the toxic effects of an anticancer drug (Ueda K. et al., Proc Natl Acad Sci U.S.A. 1987, 84: 3004-3008; Giai M. et al., Eur J Gynaecol Oncol 1991, 12: 359-373, 11). Interestingly, it was revealed by previous examination that a transcription factor, c-Jun, is a major determinant for downregulation of P-glycoprotein (Fujita T et al., Int J Cancer 2005, 117: 670-682; Miao Z H et al., Cancer Res 2003, 63: 4527-4532). REIC/Dkk-3 overexpression in MCF7/ADR cells causes c-Jun activation in a JNK-dependent manner, in a similar manner as in the case of downregulation of P-glycoprotein. Hence, it is thought that in cells to which Ad-REIC has been administered, phosphorylated c-Jun to be induced by JNK activation mediates the reverse of P-glycoprotein-dependent anti-doxorubicin resistance. This is evidenced by the result that intracellular doxorubicin accumulation in drug-resistant MCF7/ADR cells significantly increases after administration of Ad-REIC. Furthermore, with the use of another doxorubicin-(adriamycin) resistant cancer cell line (KK47/ADR (KK47/ADM) bladder cancer cells), it was confirmed that REIC/Dkk-3 overexpression due to Ad-REIC downregulated P-glycoprotein takes place in a JNK- and c-Jun-dependent manner, so as to accelerate drug resistance (Example 2). Therefore, JNK activation can be the mechanism for the effects of reversing drug resistance by administration of Ad-REIC, depending on downregulation of P-glycoprotein. However, in view of significant cell death induction after administration of Ad-REIC, cell injury itself can cause changes in the intracellular system involved in anti-cancer resistance.

In this Example, in vitro and in vivo therapeutic effects of administration of Ad-REIC on mammary cancer were demonstrated. Ad-REIC not only induces cell death but also causes cells to restore resistance to an anticancer drug, even in the case of single-agent administration. Specifically, REIC/

Dkk-3 can exert significant anti-cancer effects when used in combination with a conventionally employed anticancer drug.

EXAMPLE 2

Effects of REIC/Dkk-3 on Anticancer-Drug-Resistant Bladder Cancer Cell

An examination similar to that in Example 1 was conducted using normal bladder cancer cells and bladder cancer cells having acquired resistance to an anticancer drug.

Cell lines used herein were KK47 (KK47/Wt) which is a bladder cancer cell line and KK47/ADR (KK47/ADM) which is an anticancer drug (doxorubicin)-resistant cell line of KK47 (Kimiya K. et al., J Urol. 1992 August, 148 (2 Pt 1), 441-5; Hasegawa S. et al., Br J Cancer. 1995 May; 71 (5): 907-13) (all cells were provided by the Department of Urology, Graduate School of Medical Sciences, Kyushu University).

Figure 7:
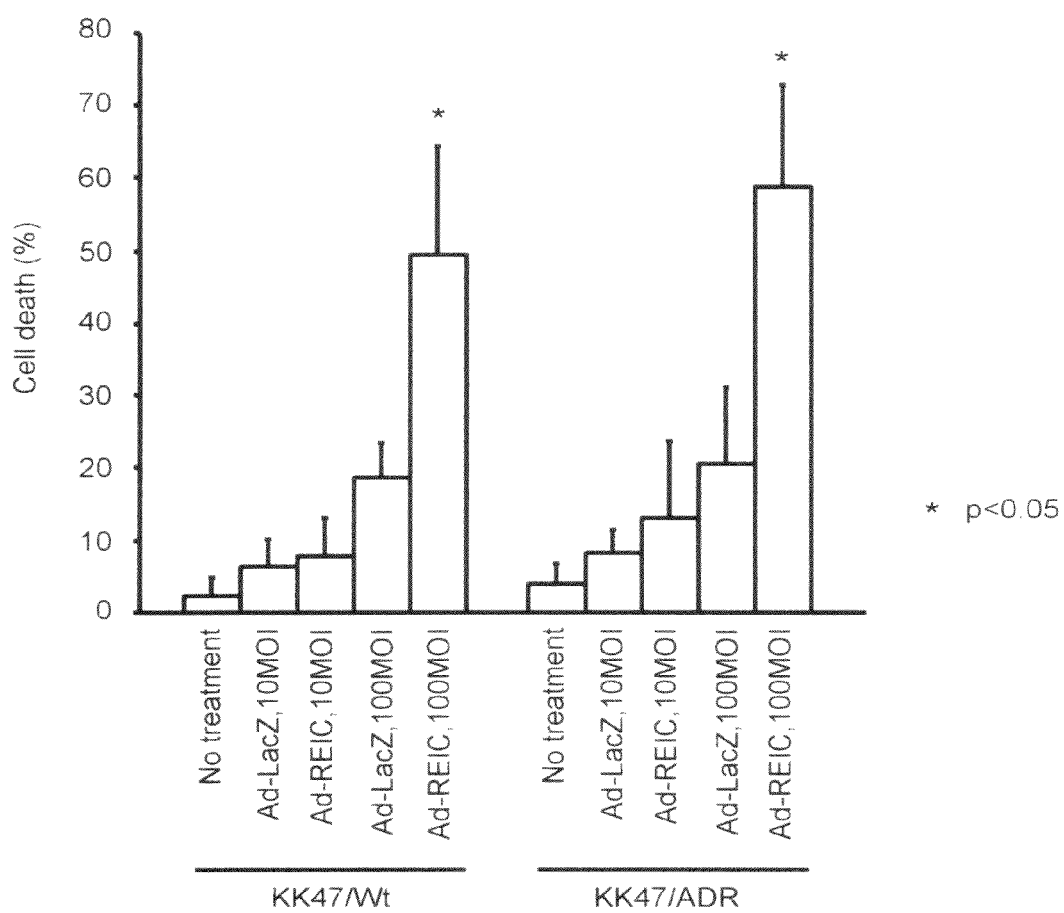
FIG. 7 shows the effects of inducing apoptosis after administration of Ad-REIC on bladder cancer cells (KK47) and its doxorubicin-resistant cells (KK47/ADR) thereof.

FIG. 7 shows the effects of inducing cell death after treatment with Ad-REIC. Cell death incidence significantly increased in KK47/Wt and KK47/ADR cells to which Ad-REIC had been administered at 100 MOI, compared with an Ad-LacZ control group.

Figure 8:
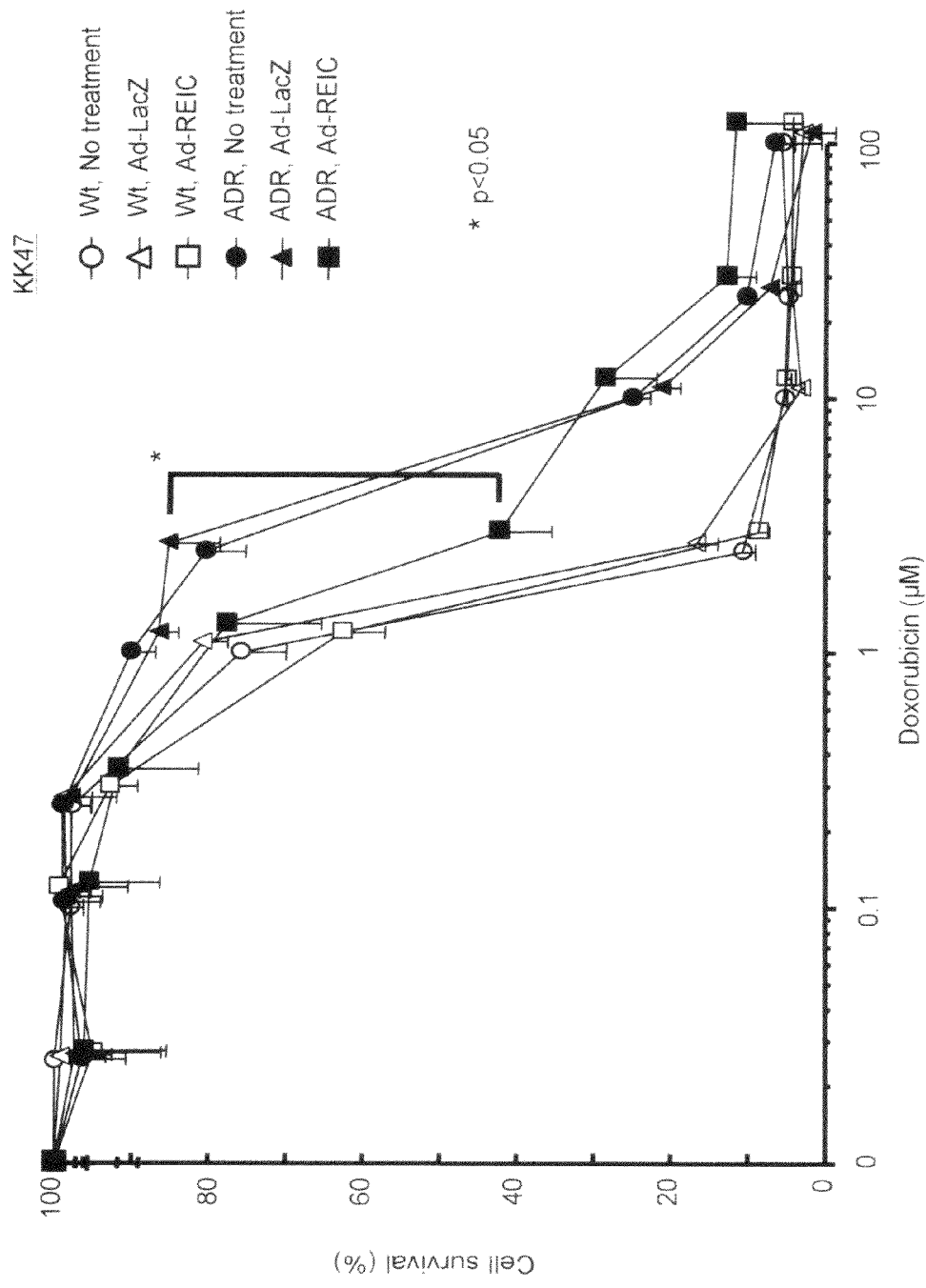
FIG. 8 shows changes in cell death sensitivity to doxorubicin in KK47/ADR cells when Ad-REIC was administered.

FIG. 8 shows changes in anticancer drug resistance after treatment with Ad-REIC. After administration of Ad-REIC at 100 MOI, cell death sensitivity to doxorubicin significantly increased.

Figure 9:
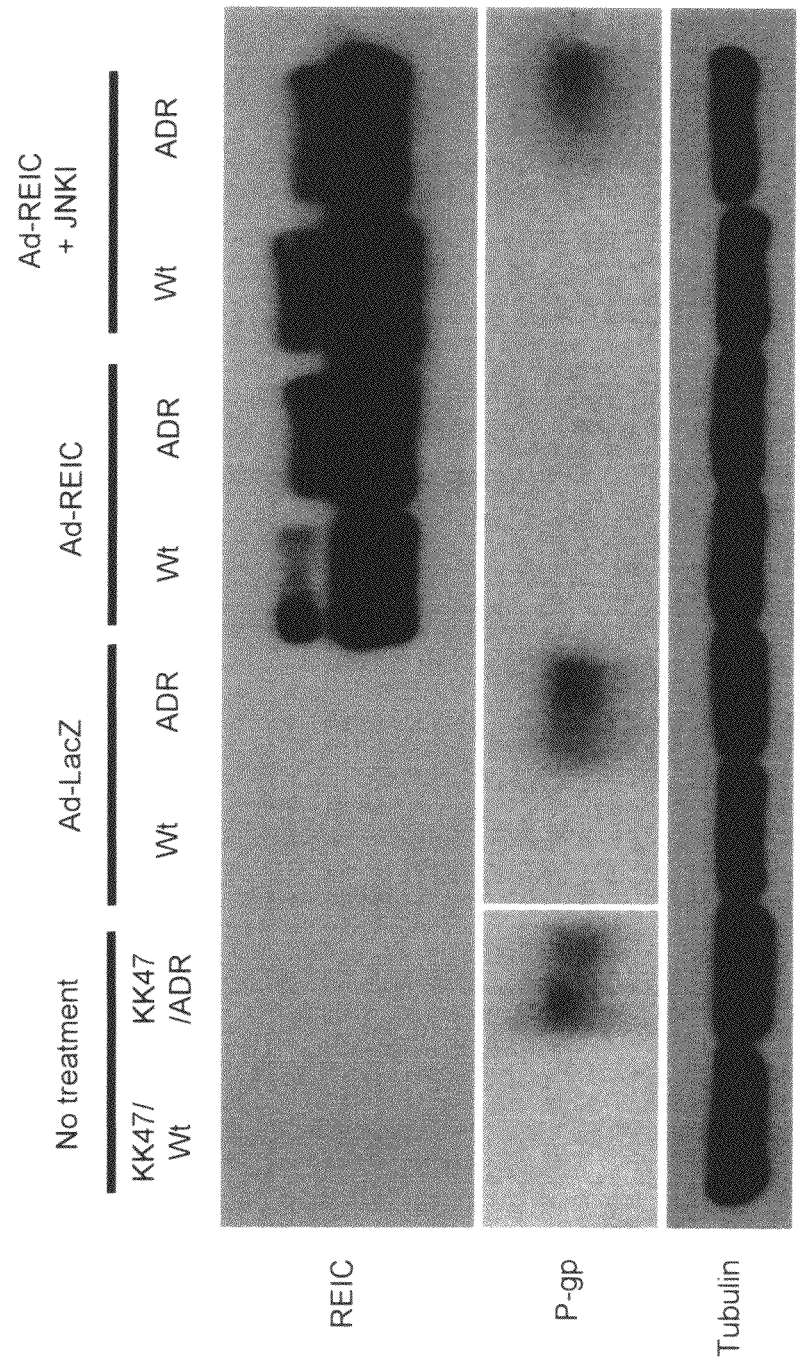
FIG. 9 shows suppressed P-glycoprotein expression resulting from administration of Ad-REIC in KK47/ADR cells.

FIG. 9 shows the suppression of P-glycoprotein expression resulting from administration of Ad-REIC. After administration of Ad-REIC at 100 MOI, P-glycoprotein expression was significantly suppressed in KK47/ADR cells. Changes in such expression were canceled by administration of an inhibitor of JNK protein.

EXAMPLE 3

Cell Death Induction by REIC/Dkk-3 DNA Fragment

PC3 ($1\times10^5$ cells) was seeded in a 6-well plate. After 24 hours, PC3 was transfected with pTracer-EF-A-1 (#1: 1-39 aa), -2 (#2: 1-78 aa), or -6 (Full: 1-350aa) plasmid, in which REIC/Dkk-3 fragment cDNA had been inserted, using a TransIT (trademark) Keratinocyte reagent (transfection reagent (Mirus Bio Corporation)). pTracer-EF-A-1 contains cDNA (cDNA comprising a sequence ranging from the $1^{st}$ nucleotide to the $117^{th}$ nucleotide of the nucleotide sequence shown in SEQ ID NO: 1) encoding a sequence ranging from the $1^{st}$ amino acid to the $39^{th}$ amino acid of the amino acid sequence shown in SEQ ID NO: 2. pTracer-EF-A-2 contains cDNA (cDNA comprising a sequence ranging from the 1st nucleotide to the $234^{th}$ nucleotide of the nucleotide sequence shown in SEQ ID NO: 1) encoding a sequence ranging from the $1^{st}$ amino acid to the $78^{th}$ amino acid of the amino acid sequence shown in SEQ ID NO: 2. pTracer-EF-A-3 contains cDNA (cDNA comprising a sequence ranging from the $1^{st}$ nucleotide to the $1050^{th}$ nucleotide of the nucleotide sequence shown in SEQ ID NO: 1) encoding a sequence ranging from the 1st amino acid to the $350^{th}$ amino acid of the amino acid sequence shown in SEQ ID NO: 2. OUMS-24 was transfected with each plasmid using FuGENE (trademark)-HD reagent (transfection reagent (Roche Applied Science)). After 48 hours, cells were subjected to nuclear staining alive using Hoechst33342 and then they were observed via a fluorescence microscope. The rate (%) of cells that had died (cells that had undergone karyopyknosis) was calculated using the case of GFP-positive cells (cells containing plasmids) as a denominator.

Figure 10:
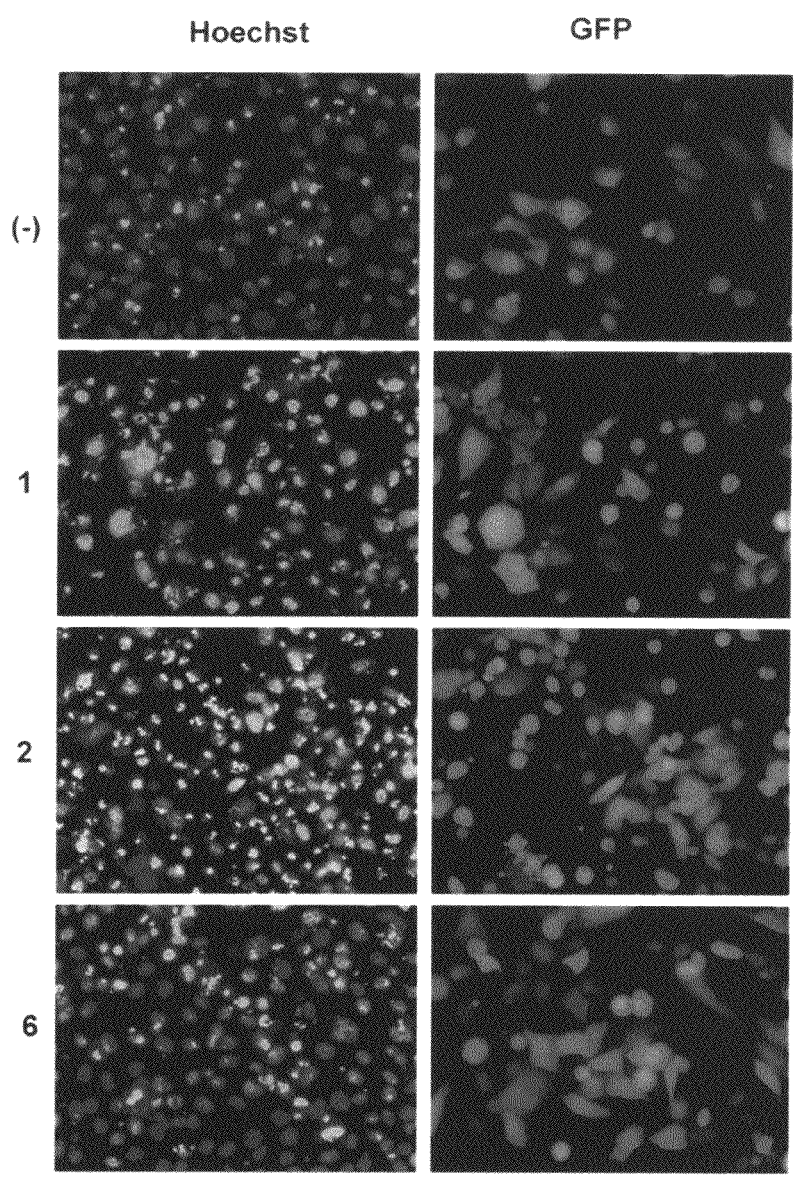
FIG. 10 shows the conditions of PC3 cell death induced by each fragment of REIC/Dkk-3 DNA.

Plasmids used for transfection of PC3 are capable of causing simultaneous expression of an inserted gene (REIC/Dkk-3 fragment) and GFP with the use of different promoters. Therefore, through detection of GFP (green), cells expressing the REIC fragment can be detected indirectly. At 48 hours after transfection, cell apoptosis induction was evaluated. FIG. 10 shows stained images. As shown in 1 and 2 of FIG. 10, cells containing nuclei (Hoechst staining: blue) that had formed aggregates (apoptosis) were observed to a significant extent among GFP-positive cells. In FIG. 10, (−) indicates empty plasmid pTracer-EF-A in which no REIC fragment had been inserted.

Figure 11:
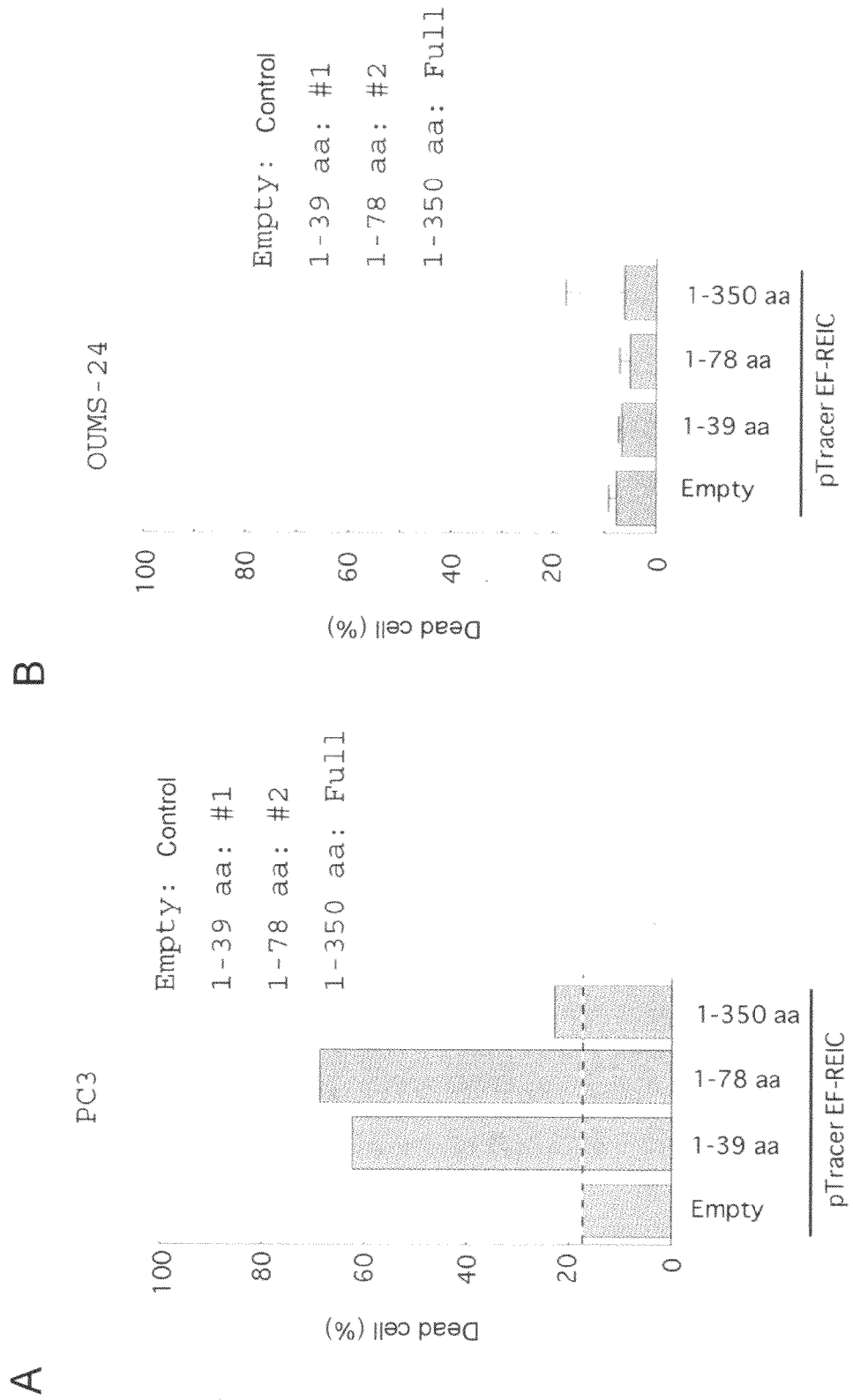
FIG. 11 shows the effects of inducing PC3 and OUMS-24 cell death induced by each fragment of REIC/Dkk-3 DNA. "A" shows the result of PC3 and "B" shows the result of OUMS-24.

FIG. 11A shows the results of calculating the rate (%) of cell death (cells that had undergone karyopyknosis) when PC3 was used, using the case of GFP-positive cells (cells containing plasmids) as a denominator. REIC fragments 1 (#1: 1-39 aa) and 2 (#2: 1-78 aa) were found to have significant cell-death-inducing effects. Meanwhile, FIG. 11B shows the results of using OUMS-24. The cell-death-inducing effects, which were observed in PC3, were not observed in normal OUMS-24 fibroblasts.

INDUSTRIAL APPLICABILITY

The cancer cell death inducing agent of the present invention, which has the effects of potentiating an anticancer drug for cancer cells having anticancer drug resistance, has cancer cell death-anti-tumor effects on anticancer-drug-resistant cancer, even in the case of single-agent administration. Furthermore, the cancer cell death inducing agent can recover the effects of an anticancer drug when it is used in combination with the anticancer drug. The cancer cell death inducing agent is a topically applicable preparation having such biphasic effects.

Cases in which the preparation of the present invention may be administered are cases of patients who have cancer lesions observed to be resistant to anticancer drug therapy. The preparation of the present invention found to exert cancer cell death tumor shrinkage effects even in the case of single-agent administration and an anticancer drug are administered in combination, so that anti-cancer effects are doubly induced and thus strong anti-tumor effects can be expected.

Strict discrimination between anticancer-drug-resistant cancer and drug-sensitive cancer is clinically difficult. The preparation of the present invention can also be expected to exert anti-cancer effects against drug-sensitive cancer. Hence, administration of the preparation at the initial stage of anticancer drug therapy becomes possible, unlike the cases of conventional techniques of attenuating P-glycoprotein expression while targeting anticancer-drug-resistant cancer. The preparation is also advantageous in that it is clinically applicable to a wide range of cases.

All publications, patents, and patent applications cited herein are incorporated herein by reference in their entirety.

The invention claimed is:

1. A method for causing a mammary cancer cell having resistance against doxorubicin to restore anticancer drug sensitivity and then inducing cancer cell death, comprising administering the following REIC/Dkk-3 DNA or a vector containing the DNA to a mammary cancer cell having resistance to doxorubicin:
(a) a DNA consisting of the nucleotide sequence shown in SEQ ID NO:1,
wherein the anticancer drug resistance is caused by upregulation of P-glycoprotein.

2. The method for inducing cancer cell death according to claim 1, wherein the vector is an adenovirus vector.

3. The method for inducing cancer cell death according to claim 1, wherein the mammary cancer cell is MCF7ADR cell.

* * * * *

SEQUENCE LISTING

<160> NUMBER OF SEQ ID NOS: 4

<210> SEQ ID NO 1
<211> LENGTH: 1053
<212> TYPE: DNA
<213> ORGANISM: Homo sapiens
<220> FEATURE:
<221> NAME/KEY: CDS
<222> LOCATION: (1)..(1053)

<400> SEQUENCE: 1

```
atg cag cgg ctt ggg gcc acc ctg ctg tgc ctg cta ctg gcg gcg gcg       48
Met Gln Arg Leu Gly Ala Thr Leu Leu Cys Leu Leu Leu Ala Ala Ala
 1               5                  10                  15 gtc ccc acg gcc ccc gcg ccc gct ccg acg gcg acc tcg gct cca gtc       96
Val Pro Thr Ala Pro Ala Pro Ala Pro Thr Ala Thr Ser Ala Pro Val
             20                  25                  30 aag ccc ggc ccg gct ctc agc tac ccg cag gag gag gcc acc ctc aat      144
Lys Pro Gly Pro Ala Leu Ser Tyr Pro Gln Glu Glu Ala Thr Leu Asn
         35                  40                  45 gag atg ttc cgc gag gtt gag gaa ctg gtg gag gac acg cag cac aaa      192
Glu Met Phe Arg Glu Val Glu Glu Leu Val Glu Asp Thr Gln His Lys
     50                  55                  60 ttg cgc agc gcg gtg gaa gag atg gag gca gaa gaa gct gct gct aaa      240
Leu Arg Ser Ala Val Glu Glu Met Glu Ala Glu Glu Ala Ala Ala Lys
 65                  70                  75                  80 gca tca tca gaa gtg aac ctg gca aac tta cct ccc agc tat cac aat      288
Ala Ser Ser Glu Val Asn Leu Ala Asn Leu Pro Pro Ser Tyr His Asn
                 85                  90                  95 gag acc aac aca gac acg aag gtt gga aat aat acc atc cat gtg cac      336
Glu Thr Asn Thr Asp Thr Lys Val Gly Asn Asn Thr Ile His Val His
            100                 105                 110 cga gaa att cac aag ata acc aac aac cag gct cga caa atg gtc ttt      384
Arg Glu Ile His Lys Ile Thr Asn Asn Gln Ala Arg Gln Met Val Phe
        115                 120                 125 tca gag aca gtt atc aca tct gtg gga gac gaa gaa ggc aga agg agc      432
Ser Glu Thr Val Ile Thr Ser Val Gly Asp Glu Glu Gly Arg Arg Ser
    130                 135                 140 cac gag tgc atc atc gac gag gac tgt ggg ccc agc atg tac tgc cag      480
His Glu Cys Ile Ile Asp Glu Asp Cys Gly Pro Ser Met Tyr Cys Gln
145                 150                 155                 160 ttt gcc agc ttc cag tac acc tgc cag cca tgc cgg ggc cag agg atg      528
Phe Ala Ser Phe Gln Tyr Thr Cys Gln Pro Cys Arg Gly Gln Arg Met
                165                 170                 175 ctc tgc acc cgg gac agt gag tgc tgt gga gac cag ctg tgt gtc tgg      576
Leu Cys Thr Arg Asp Ser Glu Cys Cys Gly Asp Gln Leu Cys Val Trp
            180                 185                 190 ggt cac tgc acc aaa atg gcc acc agg ggc agc aat ggg acc atc tgt      624
Gly His Cys Thr Lys Met Ala Thr Arg Gly Ser Asn Gly Thr Ile Cys
        195                 200                 205 gac aac cag agg gac tgc cag ccg ggg ctg tgc tgt gcc ttc cag aga      672
Asp Asn Gln Arg Asp Cys Gln Pro Gly Leu Cys Cys Ala Phe Gln Arg
    210                 215                 220 ggc ctg ctg ttc cct gtg tgc ata ccc ctg ccc gtg gag ggc gag ctt      720
Gly Leu Leu Phe Pro Val Cys Ile Pro Leu Pro Val Glu Gly Glu Leu
225                 230                 235                 240 tgc cat gac ccc gcc agc cgg ctt ctg gac ctc atc acc tgg gag cta      768
Cys His Asp Pro Ala Ser Arg Leu Leu Asp Leu Ile Thr Trp Glu Leu
                245                 250                 255 gag cct gat gga gcc ttg gac cga tgc cct tgt gcc agt ggc ctc ctc      816
Glu Pro Asp Gly Ala Leu Asp Arg Cys Pro Cys Ala Ser Gly Leu Leu
```

```
                    260                 265                 270
tgc cag ccc cac agc cac agc ctg gtg tat gtg tgc aag ccg acc ttc       864
Cys Gln Pro His Ser His Ser Leu Val Tyr Val Cys Lys Pro Thr Phe
        275                 280                 285 gtg ggg agc cgt gac caa gat ggg gag atc ctg ctg ccc aga gag gtc       912
Val Gly Ser Arg Asp Gln Asp Gly Glu Ile Leu Leu Pro Arg Glu Val
        290                 295                 300 ccc gat gag tat gaa gtt ggc agc ttc atg gag gag gtg cgc cag gag       960
Pro Asp Glu Tyr Glu Val Gly Ser Phe Met Glu Glu Val Arg Gln Glu
305                 310                 315                 320 ctg gag gac ctg gag agg agc ctg act gaa gag atg gcg ctg ggg gag      1008
Leu Glu Asp Leu Glu Arg Ser Leu Thr Glu Glu Met Ala Leu Gly Glu
                325                 330                 335 cct gcg gct gcc gcc gct gca ctg ctg gga ggg gaa gag att tag          1053
Pro Ala Ala Ala Ala Ala Leu Leu Gly Gly Glu Glu Ile
                340                 345                 350
```

<210> SEQ ID NO 2
<211> LENGTH: 350
<212> TYPE: PRT
<213> ORGANISM: Homo sapiens

<400> SEQUENCE: 2

```
Met Gln Arg Leu Gly Ala Thr Leu Leu Cys Leu Leu Leu Ala Ala Ala
1               5                   10                  15

Val Pro Thr Ala Pro Ala Pro Ala Pro Thr Ala Thr Ser Ala Pro Val
                20                  25                  30

Lys Pro Gly Pro Ala Leu Ser Tyr Pro Gln Glu Glu Ala Thr Leu Asn
            35                  40                  45

Glu Met Phe Arg Glu Val Glu Glu Leu Val Glu Asp Thr Gln His Lys
        50                  55                  60

Leu Arg Ser Ala Val Glu Glu Met Glu Ala Glu Ala Ala Ala Lys
65                  70                  75                  80

Ala Ser Ser Glu Val Asn Leu Ala Asn Leu Pro Pro Ser Tyr His Asn
                85                  90                  95

Glu Thr Asn Thr Asp Thr Lys Val Gly Asn Asn Thr Ile His Val His
                100                 105                 110

Arg Glu Ile His Lys Ile Thr Asn Asn Gln Ala Arg Gln Met Val Phe
            115                 120                 125

Ser Glu Thr Val Ile Thr Ser Val Gly Asp Glu Glu Gly Arg Arg Ser
        130                 135                 140

His Glu Cys Ile Ile Asp Glu Asp Cys Gly Pro Ser Met Tyr Cys Gln
145                 150                 155                 160

Phe Ala Ser Phe Gln Tyr Thr Cys Gln Pro Cys Arg Gly Gln Arg Met
                165                 170                 175

Leu Cys Thr Arg Asp Ser Glu Cys Cys Gly Asp Gln Leu Cys Val Trp
                180                 185                 190

Gly His Cys Thr Lys Met Ala Thr Arg Gly Ser Asn Gly Thr Ile Cys
            195                 200                 205

Asp Asn Gln Arg Asp Cys Gln Pro Gly Leu Cys Cys Ala Phe Gln Arg
        210                 215                 220

Gly Leu Leu Phe Pro Val Cys Ile Pro Leu Pro Val Glu Gly Glu Leu
225                 230                 235                 240

Cys His Asp Pro Ala Ser Arg Leu Leu Asp Leu Ile Thr Trp Glu Leu
                245                 250                 255

Glu Pro Asp Gly Ala Leu Asp Arg Cys Pro Cys Ala Ser Gly Leu Leu
```

```
                    260                 265                 270
Cys Gln Pro His Ser His Ser Leu Val Tyr Val Cys Lys Pro Thr Phe
            275                 280                 285

Val Gly Ser Arg Asp Gln Asp Gly Glu Ile Leu Leu Pro Arg Glu Val
            290                 295                 300

Pro Asp Glu Tyr Glu Val Gly Ser Phe Met Glu Glu Val Arg Gln Glu
305                 310                 315                 320

Leu Glu Asp Leu Glu Arg Ser Leu Thr Glu Glu Met Ala Leu Gly Glu
                325                 330                 335

Pro Ala Ala Ala Ala Ala Leu Leu Gly Gly Glu Glu Ile
                340                 345                 350

<210> SEQ ID NO 3
<211> LENGTH: 117
<212> TYPE: DNA
<213> ORGANISM: Homo sapiens

<400> SEQUENCE: 3
atgcagcggc ttggggccac cctgctgtgc ctgctactgg cggcggcggt ccccacggcc        60
cccgcgcccg ctccgacggc gacctcggct ccagtcaagc ccggcccggc tctcagc          117

<210> SEQ ID NO 4
<211> LENGTH: 234
<212> TYPE: DNA
<213> ORGANISM: Homo sapiens

<400> SEQUENCE: 4
atgcagcggc ttggggccac cctgctgtgc ctgctactgg cggcggcggt ccccacggcc        60
cccgcgcccg ctccgacggc gacctcggct ccagtcaagc ccggcccggc tctcagctac       120
ccgcaggagg aggccaccct caatgagatg ttccgcgagg ttgaggaact ggtggaggac       180
acgcagcaca aattgcgcag cgcggtggaa gagatggagg cagaagaagc tgct             234
```